(12) United States Patent
Werneth et al.

(10) Patent No.: US 8,486,063 B2
(45) Date of Patent: Jul. 16, 2013

(54) ABLATION CATHETER

(75) Inventors: Randell L. Werneth, San Diego, CA (US); Marshall L. Sherman, Cardiff-by-the-Sea, CA (US); Thomas M. Castellano, Temecula, CA (US); J. Christopher Flaherty, Topsfield, MA (US); Gary Edward Currie, Fallbrook, CA (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 1048 days.

(21) Appl. No.: 12/245,625

(22) Filed: Oct. 3, 2008

(65) Prior Publication Data

US 2009/0030411 A1 Jan. 29, 2009

Related U.S. Application Data

(63) Continuation of application No. 11/179,333, filed on Jul. 12, 2005.

(60) Provisional application No. 60/618,753, filed on Oct. 14, 2004.

(51) Int. Cl.
*A61B 18/18* (2006.01)

(52) U.S. Cl.
USPC .............................................. 606/41; 606/33

(58) Field of Classification Search
USPC ...................................................... 606/33, 41
See application file for complete search history.

(56) References Cited

U.S. PATENT DOCUMENTS

| | | | |
|---|---|---|---|
| 3,516,412 A | 6/1970 | Ackerman |
| 3,951,136 A | 4/1976 | Wall |
| 4,017,903 A | 4/1977 | Chu |
| 4,112,952 A | 9/1978 | Thomas et al. |
| 4,411,266 A | 10/1983 | Cosman |
| 4,432,377 A | 2/1984 | Dickhudt |
| 4,660,571 A | 4/1987 | Hess et al. |
| 4,699,147 A | 10/1987 | Chilson et al. |
| 4,785,815 A | 11/1988 | Cohen |
| 4,860,769 A | 8/1989 | Fogarty et al. |
| 4,869,248 A | 9/1989 | Narula |
| 4,882,777 A | 11/1989 | Narula |
| 4,896,671 A | 1/1990 | Cunningham et al. |
| 4,907,589 A | 3/1990 | Cosman |

(Continued)

FOREIGN PATENT DOCUMENTS

| | | |
|---|---|---|
| AU | 5200671 | 10/2005 |
| CA | 2327322 | 11/1999 |

(Continued)

OTHER PUBLICATIONS

Oral et al.; U.S. Appl. No. 11/932,378 entitled "Ablation catheters and methods for their use," filed Oct. 31, 2007.

(Continued)

*Primary Examiner* — Kevin C Sirmons
*Assistant Examiner* — Brandy S Lee
(74) *Attorney, Agent, or Firm* — Christopher & Weisberg, P.A.

(57) ABSTRACT

Devices, systems and methods are disclosed for the ablation of tissue. Embodiments include an ablation catheter which has an array of ablation elements attached to a deployable carrier assembly. The carrier assembly can be constrained within the lumen of a catheter, and deployed to take on an expanded condition.

10 Claims, 8 Drawing Sheets

U.S. PATENT DOCUMENTS

| | | | |
|---|---|---|---|
| 4,920,980 A | 5/1990 | Jackowski |
| 4,940,064 A | 7/1990 | Desai |
| 4,966,597 A | 10/1990 | Cosman |
| 5,010,894 A | 4/1991 | Edhag |
| 5,016,808 A | 5/1991 | Heil, Jr. et al. |
| 5,083,565 A | 1/1992 | Parins |
| 5,100,423 A | 3/1992 | Fearnot |
| 5,156,151 A | 10/1992 | Imran |
| 5,184,621 A | 2/1993 | Vogel et al. |
| 5,215,103 A | 6/1993 | Desai |
| 5,228,442 A | 7/1993 | Imran |
| 5,230,349 A | 7/1993 | Langberg |
| 5,231,987 A | 8/1993 | Robson |
| 5,231,995 A | 8/1993 | Desai |
| 5,234,004 A | 8/1993 | Hascoet et al. |
| 5,239,999 A | 8/1993 | Imran |
| 5,255,679 A | 10/1993 | Imran |
| 5,279,299 A | 1/1994 | Imran |
| 5,281,213 A | 1/1994 | Milder et al. |
| 5,281,218 A | 1/1994 | Imran |
| 5,309,910 A | 5/1994 | Edwards et al. |
| 5,313,943 A | 5/1994 | Houser et al. |
| 5,318,525 A | 6/1994 | West et al. |
| 5,324,284 A | 6/1994 | Imran |
| 5,327,889 A | 7/1994 | Imran |
| 5,330,466 A | 7/1994 | Imran |
| 5,334,193 A | 8/1994 | Nardella |
| 5,342,295 A | 8/1994 | Imran |
| 5,342,357 A | 8/1994 | Nardella |
| 5,345,936 A | 9/1994 | Pomeranz et al. |
| 5,348,554 A | 9/1994 | Imran et al. |
| D351,652 S | 10/1994 | Thompson et al. |
| 5,364,352 A | 11/1994 | Cimino et al. |
| 5,365,926 A | 11/1994 | Desai |
| 5,370,644 A | 12/1994 | Langberg |
| 5,383,852 A | 1/1995 | Stevens-Wright |
| 5,383,917 A | 1/1995 | Desai et al. |
| 5,391,147 A | 2/1995 | Imran et al. |
| 5,397,304 A | 3/1995 | Truckai |
| 5,397,339 A | 3/1995 | Desai |
| 5,400,783 A | 3/1995 | Pomeranz et al. |
| 5,404,638 A | 4/1995 | Imran |
| 5,406,946 A | 4/1995 | Imran |
| 5,411,025 A | 5/1995 | Webster, Jr. |
| 5,423,808 A | 6/1995 | Edwards et al. |
| 5,423,811 A | 6/1995 | Imran et al. |
| 5,433,198 A | 7/1995 | Desai |
| 5,433,739 A | 7/1995 | Sluijter et al. |
| 5,445,148 A | 8/1995 | Jaraczewski et al. |
| 5,462,521 A | 10/1995 | Brucker et al. |
| 5,462,545 A | 10/1995 | Wang et al. |
| 5,465,717 A | 11/1995 | Imran et al. |
| 5,471,982 A | 12/1995 | Edwards et al. |
| 5,487,757 A | 1/1996 | Truckai et al. |
| 5,492,119 A | 2/1996 | Abrams |
| 5,500,011 A | 3/1996 | Desai |
| 5,507,802 A | 4/1996 | Imran |
| 5,509,411 A | 4/1996 | Littmann et al. |
| 5,527,279 A | 6/1996 | Imran |
| 5,533,967 A | 7/1996 | Imran |
| 5,536,267 A | 7/1996 | Edwards et al. |
| 5,540,681 A | 7/1996 | Strul et al. |
| 5,545,161 A | 8/1996 | Imran |
| 5,545,193 A | 8/1996 | Fleischman et al. |
| 5,545,200 A | 8/1996 | West et al. |
| 5,558,073 A | 9/1996 | Pomeranz et al. |
| 5,562,720 A * | 10/1996 | Stern et al. ............ 607/98 |
| 5,573,533 A | 11/1996 | Strul |
| 5,575,766 A | 11/1996 | Swartz et al. |
| 5,575,810 A | 11/1996 | Swanson et al. |
| 5,578,007 A | 11/1996 | Imran |
| 5,582,609 A | 12/1996 | Swanson et al. |
| 5,584,830 A | 12/1996 | Ladd et al. |
| 5,588,432 A | 12/1996 | Crowley |
| 5,588,964 A | 12/1996 | Imran et al. |
| 5,595,183 A | 1/1997 | Swanson et al. |
| 5,596,995 A | 1/1997 | Sherman et al. |
| 5,598,848 A | 2/1997 | Swanson et al. |
| 5,601,088 A | 2/1997 | Swanson et al. |
| 5,606,974 A | 3/1997 | Castellano et al. |
| 5,607,462 A | 3/1997 | Imran |
| 5,620,481 A | 4/1997 | Desai et al. |
| 5,626,136 A | 5/1997 | Webster, Jr. |
| 5,630,425 A | 5/1997 | Panescu et al. |
| 5,630,837 A | 5/1997 | Crowley |
| 5,637,090 A | 6/1997 | McGee et al. |
| D381,076 S | 7/1997 | Thornton et al. |
| 5,645,064 A | 7/1997 | Littmann et al. |
| 5,645,082 A | 7/1997 | Sung et al. |
| 5,651,780 A | 7/1997 | Jackson et al. |
| 5,656,029 A | 8/1997 | Imran et al. |
| 5,657,755 A | 8/1997 | Desai |
| 5,658,278 A | 8/1997 | Imran et al. |
| 5,662,606 A | 9/1997 | Cimino et al. |
| 5,666,970 A | 9/1997 | Smith |
| 5,673,695 A * | 10/1997 | McGee et al. ............ 600/374 |
| 5,680,860 A | 10/1997 | Imran |
| 5,681,280 A | 10/1997 | Rusk et al. |
| 5,682,885 A | 11/1997 | Littmann et al. |
| 5,685,322 A | 11/1997 | Sung et al. |
| 5,687,723 A | 11/1997 | Avitall |
| 5,693,078 A | 12/1997 | Desai et al. |
| 5,697,927 A | 12/1997 | Imran et al. |
| 5,697,928 A | 12/1997 | Walcott et al. |
| 5,699,796 A | 12/1997 | Littmann et al. |
| 5,702,438 A | 12/1997 | Avitall |
| 5,704,791 A | 1/1998 | Gillio |
| 5,706,809 A | 1/1998 | Littmann et al. |
| 5,711,298 A | 1/1998 | Littmann et al. |
| 5,716,389 A | 2/1998 | Walinsky et al. |
| 5,722,401 A | 3/1998 | Pietroski et al. |
| 5,722,975 A | 3/1998 | Edwards et al. |
| 5,724,985 A | 3/1998 | Snell et al. |
| 5,733,323 A | 3/1998 | Buck et al. |
| 5,735,280 A | 4/1998 | Sherman et al. |
| 5,741,320 A | 4/1998 | Thornton et al. |
| 5,766,152 A | 6/1998 | Morley et al. |
| 5,769,791 A | 6/1998 | Benaron et al. |
| 5,769,847 A | 6/1998 | Panescu et al. |
| 5,772,590 A | 6/1998 | Webster, Jr. |
| 5,775,327 A | 7/1998 | Randolph et al. |
| 5,782,239 A | 7/1998 | Webster, Jr. |
| 5,782,760 A | 7/1998 | Schaer |
| 5,782,828 A | 7/1998 | Chen et al. |
| 5,782,899 A | 7/1998 | Imran |
| 5,792,140 A | 8/1998 | Tu et al. |
| 5,800,482 A | 9/1998 | Pomeranz et al. |
| 5,810,740 A | 9/1998 | Paisner |
| 5,820,568 A | 10/1998 | Willis |
| 5,827,272 A | 10/1998 | Breining et al. |
| 5,837,001 A | 11/1998 | Mackey |
| 5,849,028 A | 12/1998 | Chen |
| 5,857,464 A | 1/1999 | Desai |
| 5,857,997 A | 1/1999 | Cimino et al. |
| 5,860,920 A | 1/1999 | McGee et al. |
| 5,863,291 A | 1/1999 | Schaer |
| 5,871,523 A | 2/1999 | Fleischman et al. |
| 5,873,865 A | 2/1999 | Horzewski et al. |
| 5,876,399 A | 3/1999 | Chia et al. |
| 5,881,732 A | 3/1999 | Sung et al. |
| 5,882,333 A | 3/1999 | Schaer et al. |
| 5,885,278 A | 3/1999 | Fleischman |
| 5,891,027 A | 4/1999 | Tu et al. |
| 5,891,135 A | 4/1999 | Jackson et al. |
| 5,891,137 A | 4/1999 | Chia et al. |
| 5,891,138 A | 4/1999 | Tu et al. |
| 5,893,847 A | 4/1999 | Kordis |
| 5,893,884 A | 4/1999 | Tu |
| 5,893,885 A | 4/1999 | Webster, Jr. |
| 5,895,355 A | 4/1999 | Schaer |
| 5,895,417 A | 4/1999 | Pomeranz et al. |
| 5,897,554 A | 4/1999 | Chia et al. |
| 5,904,680 A | 5/1999 | Kordis et al. |
| 5,906,605 A | 5/1999 | Coxum |
| 5,910,129 A | 6/1999 | Koblish et al. |
| 5,911,720 A | 6/1999 | Bourne et al. |
| 5,913,854 A | 6/1999 | Maguire et al. |

| | | | | | | |
|---|---|---|---|---|---|---|
| 5,916,214 A | 6/1999 | Cosio et al. | | 6,245,067 B1 | 6/2001 | Tu et al. |
| 5,928,191 A | 7/1999 | Houser et al. | | 6,245,089 B1 | 6/2001 | Daniel et al. |
| 5,931,835 A | 8/1999 | Mackey | | 6,251,107 B1 | 6/2001 | Schaer |
| 5,935,063 A | 8/1999 | Nguyen | | 6,256,540 B1 | 7/2001 | Panescu et al. |
| 5,938,694 A | 8/1999 | Jaraczewski et al. | | 6,264,653 B1 | 7/2001 | Falwell |
| 5,941,845 A | 8/1999 | Tu et al. | | 6,264,664 B1 | 7/2001 | Avellanet |
| 5,951,471 A | 9/1999 | de la Rama et al. | | 6,267,746 B1 | 7/2001 | Bumbalough |
| 5,954,719 A | 9/1999 | Chen et al. | | 6,290,697 B1 | 9/2001 | Tu et al. |
| 5,957,842 A | 9/1999 | Littmann et al. | | 6,293,943 B1 | 9/2001 | Panescu et al. |
| 5,960,796 A | 10/1999 | Sung et al. | | 6,302,880 B1 | 10/2001 | Schaer |
| 5,967,978 A | 10/1999 | Littmann et al. | | 6,309,385 B1 | 10/2001 | Simpson |
| 5,968,040 A | 10/1999 | Swanson et al. | | 6,312,425 B1 | 11/2001 | Simpson et al. |
| 5,971,980 A | 10/1999 | Sherman | | 6,319,251 B1 | 11/2001 | Tu et al. |
| 5,992,418 A | 11/1999 | de la Rama et al. | | 6,325,797 B1 | 12/2001 | Stewart et al. |
| 5,997,532 A | 12/1999 | McLaughlin et al. | | 6,332,880 B1 | 12/2001 | Yang et al. |
| 6,001,093 A | 12/1999 | Swanson et al. | | 6,332,881 B1 | 12/2001 | Carner et al. |
| 6,001,095 A | 12/1999 | de la Rama et al. | | 6,346,104 B2 | 2/2002 | Daly et al. |
| 6,002,956 A | 12/1999 | Schaer | | 6,353,751 B1 | 3/2002 | Swanson |
| 6,004,269 A | 12/1999 | Crowley et al. | | 6,360,128 B2 | 3/2002 | Kordis et al. |
| 6,014,581 A | 1/2000 | Whayne et al. | | 6,370,435 B2 | 4/2002 | Panescu et al. |
| 6,021,340 A | 2/2000 | Randolph et al. | | 6,371,955 B1 | 4/2002 | Fuimaono et al. |
| 6,023,638 A | 2/2000 | Swanson | | 6,379,352 B1 | 4/2002 | Reynolds et al. |
| 6,029,091 A | 2/2000 | de la Rama et al. | | 6,389,311 B1 | 5/2002 | Whayne et al. |
| 6,032,674 A | 3/2000 | Eggers et al. | | 6,391,024 B1 | 5/2002 | Sun et al. |
| 6,033,403 A | 3/2000 | Tu et al. | | 6,425,894 B1 | 7/2002 | Brucker et al. |
| 6,042,580 A | 3/2000 | Simpson | | 6,428,536 B2 | 8/2002 | Panescu et al. |
| 6,045,550 A | 4/2000 | Simpson et al. | | 6,428,537 B1 | 8/2002 | Swanson et al. |
| 6,048,329 A | 4/2000 | Thompson et al. | | 6,440,129 B1 | 8/2002 | Simpson |
| 6,049,737 A | 4/2000 | Simpson et al. | | 6,447,506 B1 | 9/2002 | Swanson et al. |
| 6,050,994 A | 4/2000 | Sherman | | 6,451,015 B1 | 9/2002 | Rittman, III et al. |
| 6,052,612 A | 4/2000 | Desai | | 6,454,758 B1 | 9/2002 | Thompson et al. |
| 6,053,937 A | 4/2000 | Edwards et al. | | 6,456,864 B1 | 9/2002 | Swanson et al. |
| 6,056,744 A | 5/2000 | Edwards | | 6,460,545 B2 | 10/2002 | Kordis |
| 6,059,778 A | 5/2000 | Sherman | | 6,471,693 B1 | 10/2002 | Carroll et al. |
| 6,063,077 A | 5/2000 | Schaer | | 6,471,699 B1 | 10/2002 | Fleischman et al. |
| 6,063,082 A | 5/2000 | DeVore et al. | | 6,475,213 B1 | 11/2002 | Whayne et al. |
| 6,064,902 A | 5/2000 | Haissaguerre et al. | | 6,475,214 B1 | 11/2002 | Moaddeb |
| 6,068,629 A | 5/2000 | Haissaguerre et al. | | 6,477,396 B1 | 11/2002 | Mest et al. |
| 6,070,094 A | 5/2000 | Swanson et al. | | 6,478,793 B1 | 11/2002 | Cosman et al. |
| 6,071,274 A | 6/2000 | Thompson et al. | | 6,485,487 B1 | 11/2002 | Sherman |
| 6,071,279 A | 6/2000 | Whayne et al. | | 6,487,441 B1 | 11/2002 | Swanson et al. |
| 6,071,281 A | 6/2000 | Burnside et al. | | 6,488,678 B2 | 12/2002 | Sherman |
| 6,071,282 A | 6/2000 | Fleischman | | 6,490,468 B2 | 12/2002 | Panescu et al. |
| 6,074,351 A | 6/2000 | Houser | | 6,493,586 B1 | 12/2002 | Stahmann et al. |
| 6,086,581 A | 7/2000 | Reynolds et al. | | 6,500,167 B1 | 12/2002 | Webster, Jr. |
| 6,088,610 A | 7/2000 | Littmann et al. | | 6,500,172 B1 | 12/2002 | Panescu et al. |
| 6,096,036 A | 8/2000 | Bowe et al. | | 6,514,246 B1 | 2/2003 | Swanson et al. |
| 6,099,524 A | 8/2000 | Lipson et al. | | 6,517,536 B2 | 2/2003 | Hooven et al. |
| 6,106,522 A | 8/2000 | Fleischman et al. | | 6,522,905 B2 | 2/2003 | Desai |
| 6,107,699 A | 8/2000 | Swanson | | 6,529,756 B1 | 3/2003 | Phan et al. |
| 6,115,626 A | 9/2000 | Whayne et al. | | 6,530,922 B2 | 3/2003 | Cosman et al. |
| 6,119,041 A | 9/2000 | Pomeranz et al. | | 6,540,744 B2 | 4/2003 | Hassett et al. |
| 6,120,476 A | 9/2000 | Fung et al. | | 6,542,773 B2 | 4/2003 | Dupree et al. |
| 6,129,724 A | 10/2000 | Fleischman et al. | | 6,544,262 B2 | 4/2003 | Fleischman |
| 6,141,576 A | 10/2000 | Littmann et al. | | 6,551,271 B2 | 4/2003 | Nguyen |
| 6,146,379 A | 11/2000 | Fleischman et al. | | 6,554,794 B1 | 4/2003 | Mueller et al. |
| 6,146,381 A | 11/2000 | Bowe et al. | | 6,558,378 B2 | 5/2003 | Sherman et al. |
| 6,165,169 A | 12/2000 | Panescu et al. | | 6,565,511 B2 | 5/2003 | Panescu et al. |
| 6,167,291 A | 12/2000 | Barajas et al. | | 6,569,114 B2 | 5/2003 | Ponzi et al. |
| 6,171,305 B1 | 1/2001 | Sherman | | 6,569,162 B2 | 5/2003 | He |
| 6,171,306 B1 | 1/2001 | Swanson et al. | | 6,569,163 B2 | 5/2003 | Hata et al. |
| 6,179,833 B1 | 1/2001 | Taylor | | 6,572,612 B2 | 6/2003 | Stewart et al. |
| 6,200,314 B1 | 3/2001 | Sherman | | 6,574,492 B1 | 6/2003 | Ben-Haim et al. |
| 6,212,426 B1 | 4/2001 | Swanson | | 6,575,997 B1 | 6/2003 | Palmer et al. |
| 6,214,002 B1 | 4/2001 | Fleischman et al. | | 6,583,796 B2 | 6/2003 | Jamar et al. |
| 6,216,043 B1 | 4/2001 | Swanson et al. | | 6,597,955 B2 | 7/2003 | Panescu et al. |
| 6,216,044 B1 | 4/2001 | Kordis | | 6,602,242 B1 | 8/2003 | Fung et al. |
| 6,217,573 B1 | 4/2001 | Webster | | 6,605,087 B2 | 8/2003 | Swartz et al. |
| 6,217,576 B1 | 4/2001 | Tu et al. | | 6,607,505 B1 | 8/2003 | Thompson et al. |
| 6,226,542 B1 | 5/2001 | Reisfeld | | 6,607,520 B2 | 8/2003 | Keane |
| 6,231,570 B1 | 5/2001 | Tu et al. | | 6,616,657 B2 | 9/2003 | Simpson et al. |
| 6,238,390 B1 | 5/2001 | Tu et al. | | 6,625,482 B1 | 9/2003 | Panescu et al. |
| 6,241,666 B1 | 6/2001 | Pomeranz et al. | | 6,628,976 B1 | 9/2003 | Fuimaono et al. |
| 6,241,724 B1 | 6/2001 | Fleischman et al. | | 6,632,223 B1 | 10/2003 | Keane |
| 6,241,725 B1 | 6/2001 | Cosman | | 6,635,056 B2 | 10/2003 | Kadhiresan et al. |
| 6,241,726 B1 | 6/2001 | Raymond et al. | | 6,638,223 B2 | 10/2003 | Lifshitz et al. |
| 6,241,727 B1 | 6/2001 | Tu et al. | | 6,638,275 B1 | 10/2003 | McGaffigan et al. |
| 6,241,728 B1 | 6/2001 | Gaiser et al. | | 6,640,120 B1 | 10/2003 | Swanson et al. |
| 6,241,754 B1 | 6/2001 | Swanson et al. | | 6,652,513 B2 | 11/2003 | Panescu et al. |

| Patent Number | Date | Inventor |
|---|---|---|
| 6,652,517 B1 | 11/2003 | Hall et al. |
| 6,658,279 B2 | 12/2003 | Swanson et al. |
| 6,669,692 B1 | 12/2003 | Nelson et al. |
| 6,669,693 B2 | 12/2003 | Friedman |
| 6,671,533 B2 | 12/2003 | Chen et al. |
| 6,673,290 B1 | 1/2004 | Whayne et al. |
| 6,690,972 B2 | 2/2004 | Conley et al. |
| 6,701,180 B1 | 3/2004 | Desai |
| 6,702,811 B2 | 3/2004 | Stewart et al. |
| 6,711,428 B2 | 3/2004 | Fuimaono et al. |
| 6,730,078 B2 | 5/2004 | Simpson et al. |
| 6,738,673 B2 | 5/2004 | Desai |
| 6,740,080 B2 | 5/2004 | Jain et al. |
| 6,743,225 B2 | 6/2004 | Sanchez et al. |
| 6,746,446 B1 | 6/2004 | Hill, III et al. |
| 6,752,804 B2 | 6/2004 | Simpson et al. |
| 6,761,716 B2 | 7/2004 | Kadhiresan et al. |
| 6,805,131 B2 | 10/2004 | Kordis |
| 6,813,520 B2 | 11/2004 | Truckai et al. |
| 6,814,732 B2 | 11/2004 | Schaer |
| 6,830,576 B2 | 12/2004 | Fleischman et al. |
| 6,866,662 B2 | 3/2005 | Fuimaono et al. |
| 6,893,438 B2 | 5/2005 | Hall et al. |
| 6,893,439 B2 | 5/2005 | Fleischman |
| 6,893,442 B2 | 5/2005 | Whayne |
| 6,916,306 B1 | 7/2005 | Jenkins et al. |
| 6,936,047 B2 | 8/2005 | Nasab et al. |
| 6,939,349 B2 | 9/2005 | Fleischman et al. |
| 6,952,615 B2 | 10/2005 | Satake |
| 6,955,173 B2 | 10/2005 | Lesh |
| 6,960,206 B2 | 11/2005 | Keane |
| 6,961,602 B2 | 11/2005 | Fuimaono et al. |
| 6,964,660 B2 | 11/2005 | Maguire et al. |
| 6,966,908 B2 | 11/2005 | Maguire et al. |
| 6,972,016 B2 | 12/2005 | Hill, III et al. |
| 6,973,339 B2 | 12/2005 | Govari |
| 6,987,995 B2 | 1/2006 | Drysen |
| 7,001,336 B2 | 2/2006 | Mandrusov et al. |
| 7,025,766 B2 | 4/2006 | Whayne et al. |
| 7,029,470 B2 | 4/2006 | Francischelli et al. |
| 7,029,471 B2 | 4/2006 | Thompson et al. |
| 7,044,135 B2 | 5/2006 | Lesh |
| 7,047,068 B2 | 5/2006 | Haissaguerre |
| 7,048,734 B1 | 5/2006 | Fleischman et al. |
| 7,048,756 B2 | 5/2006 | Eggers et al. |
| 7,077,823 B2 | 7/2006 | McDaniel |
| 7,094,235 B2 | 8/2006 | Francischelli |
| 7,099,711 B2 | 8/2006 | Fuimaono et al. |
| 7,099,712 B2 | 8/2006 | Fuimaono et al. |
| 7,113,831 B2 | 9/2006 | Hooven |
| 7,115,122 B1 | 10/2006 | Swanson et al. |
| 7,118,568 B2 | 10/2006 | Hassett et al. |
| 7,122,031 B2 | 10/2006 | Edwards et al. |
| 7,151,964 B2 | 12/2006 | Desai et al. |
| 7,155,270 B2 | 12/2006 | Solis et al. |
| 7,156,843 B2 | 1/2007 | Skarda |
| 7,163,537 B2 | 1/2007 | Lee et al. |
| 2001/0029366 A1 | 10/2001 | Swanson et al. |
| 2001/0039415 A1 | 11/2001 | Francischelli et al. |
| 2001/0044625 A1 | 11/2001 | Hata et al. |
| 2001/0051803 A1 | 12/2001 | Desai et al. |
| 2002/0065465 A1 | 5/2002 | Panescu et al. |
| 2002/0120263 A1 | 8/2002 | Brown et al. |
| 2002/0126036 A1 | 9/2002 | Flaherty et al. |
| 2002/0148476 A1 | 10/2002 | Farley et al. |
| 2002/0161422 A1 | 10/2002 | Swanson et al. |
| 2003/0018330 A1 | 1/2003 | Swanson et al. |
| 2003/0093069 A1 | 5/2003 | Panescu et al. |
| 2003/0125730 A1 | 7/2003 | Berube et al. |
| 2003/0181819 A1 | 9/2003 | Desai |
| 2003/0195407 A1 | 10/2003 | Fuimaono et al. |
| 2003/0195501 A1 | 10/2003 | Sherman et al. |
| 2003/0199746 A1 | 10/2003 | Fuimaono et al. |
| 2003/0204185 A1 | 10/2003 | Sherman et al. |
| 2003/0204186 A1 | 10/2003 | Geistert |
| 2004/0015164 A1 | 1/2004 | Fuimaono et al. |
| 2004/0044270 A1 | 3/2004 | Barry |
| 2004/0082947 A1 | 4/2004 | Oral et al. |
| 2004/0116921 A1 | 6/2004 | Sherman et al. |
| 2004/0133154 A1 | 7/2004 | Flaherty et al. |
| 2004/0138545 A1 | 7/2004 | Chen et al. |
| 2004/0143256 A1 | 7/2004 | Bednarek |
| 2004/0147827 A1 | 7/2004 | Bowe |
| 2004/0152980 A1 | 8/2004 | Desai |
| 2004/0158141 A1 | 8/2004 | Scheib |
| 2004/0181139 A1 | 9/2004 | Falwell et al. |
| 2004/0181249 A1 | 9/2004 | Torrance et al. |
| 2004/0182384 A1 | 9/2004 | Alfery |
| 2004/0220625 A1 | 11/2004 | Silvestri et al. |
| 2004/0230227 A1 | 11/2004 | Avrahami et al. |
| 2004/0236324 A1 | 11/2004 | Muller et al. |
| 2004/0247164 A1 | 12/2004 | Furnish |
| 2005/0010095 A1 | 1/2005 | Stewart et al. |
| 2005/0010206 A1* | 1/2005 | Nasab et al. .................... 606/41 |
| 2005/0015084 A1 | 1/2005 | Hill et al. |
| 2005/0033137 A1 | 2/2005 | Oral et al. |
| 2005/0033315 A1 | 2/2005 | Hankins |
| 2005/0065512 A1 | 3/2005 | Schaer |
| 2005/0096644 A1 | 5/2005 | Hall et al. |
| 2005/0101946 A1 | 5/2005 | Govari et al. |
| 2005/0119651 A1 | 6/2005 | Fuimaono et al. |
| 2005/0148892 A1 | 7/2005 | Desai |
| 2005/0177146 A1 | 8/2005 | Sherman |
| 2005/0187545 A1 | 8/2005 | Hooven et al. |
| 2005/0234439 A1 | 10/2005 | Underwood |
| 2005/0234444 A1 | 10/2005 | Hooven |
| 2005/0240176 A1 | 10/2005 | Oral et al. |
| 2005/0251132 A1 | 11/2005 | Oral et al. |
| 2005/0256521 A1 | 11/2005 | Kozel |
| 2006/0030844 A1 | 2/2006 | Knight et al. |
| 2006/0084966 A1 | 4/2006 | Maguire et al. |
| 2006/0089637 A1 | 4/2006 | Werneth et al. |
| 2006/0106375 A1 | 5/2006 | Werneth et al. |
| 2006/0111700 A1 | 5/2006 | Kunis et al. |
| 2006/0111701 A1 | 5/2006 | Oral et al. |
| 2006/0111702 A1 | 5/2006 | Oral et al. |
| 2006/0111703 A1 | 5/2006 | Kunis et al. |
| 2006/0111708 A1 | 5/2006 | Vanney et al. |
| 2006/0142753 A1 | 6/2006 | Francischelli et al. |
| 2006/0167448 A1 | 7/2006 | Kozel |
| 2006/0189975 A1 | 8/2006 | Whayne et al. |
| 2006/0195082 A1 | 8/2006 | Francischelli |
| 2006/0206109 A1 | 9/2006 | Swanson |
| 2006/0241366 A1 | 10/2006 | Falwell et al. |
| 2007/0027448 A1 | 2/2007 | Paul et al. |
| 2007/0083193 A1 | 4/2007 | Werneth et al. |
| 2007/0083194 A1 | 4/2007 | Kunis et al. |
| 2007/0083195 A1 | 4/2007 | Werneth et al. |
| 2007/0106293 A1 | 5/2007 | Oral et al. |
| 2009/0030411 A1 | 1/2009 | Werneth et al. |

FOREIGN PATENT DOCUMENTS

| | | |
|---|---|---|
| CA | 2327518 | 11/1999 |
| CA | 2328064 | 11/1999 |
| CA | 2328070 | 11/1999 |
| CA | 2371935 | 12/2000 |
| CA | 2222617 C | 7/2002 |
| CA | 2437140 | 6/2004 |
| CA | 2492283 | 7/2005 |
| CA | 2194061 C | 4/2006 |
| CA | 2276755 C | 5/2006 |
| CA | 2251041 C | 6/2006 |
| EP | 0428812 A1 | 5/1991 |
| EP | 0598742 A1 | 1/1993 |
| EP | 428812 B1 | 3/1995 |
| EP | 779059 A | 6/1997 |
| EP | 0779059 A1 | 6/1997 |
| EP | 598742 B1 | 8/1999 |
| EP | 879016 B1 | 10/2003 |
| EP | 1360938 A1 | 11/2003 |
| EP | 1364677 A2 | 11/2003 |
| EP | 1554986 A1 | 7/2005 |
| EP | 823843 B1 | 10/2005 |
| EP | 1384445 B1 | 2/2006 |
| EP | 1169976 B1 | 4/2006 |
| EP | 1415680 B1 | 4/2006 |
| EP | 1011437 B1 | 5/2006 |
| EP | 1210021 B1 | 5/2006 |

| | | | |
|---|---|---|---|
| EP | 1125549 B1 | 6/2006 | |
| EP | 1182980 B1 | 6/2006 | |
| EP | 1207798 B1 | 6/2006 | |
| EP | 1321166 B1 | 7/2006 | |
| EP | 1343427 B1 | 7/2006 | |
| EP | 828451 B1 | 9/2006 | |
| EP | 1070480 B1 | 9/2006 | |
| EP | 1014874 B1 | 12/2006 | |
| EP | 1383437 B1 | 12/2006 | |
| EP | 1455667 B1 | 1/2007 | |
| EP | 957794 B1 | 7/2007 | |
| JP | 2004188179 A | 7/2004 | |
| SU | 1512622 A1 | 10/1989 | |
| SU | 1544396 A1 | 2/1990 | |
| SU | 1690786 A1 | 11/1991 | |
| WO | 9006079 A1 | 6/1990 | |
| WO | WO90/06079 A1 | 6/1990 | |
| WO | WO93/08756 A1 | 5/1993 | |
| WO | WO93/25273 A1 | 12/1993 | |
| WO | WO94/12098 A1 | 6/1994 | |
| WO | WO96/10961 A1 | 4/1996 | |
| WO | WO96/32885 A1 | 10/1996 | |
| WO | WO96/32897 A1 | 10/1996 | |
| WO | WO96/34558 A1 | 11/1996 | |
| WO | WO96/34559 A1 | 11/1996 | |
| WO | WO96/34560 A1 | 11/1996 | |
| WO | WO96/34567 A1 | 11/1996 | |
| WO | WO96/34569 A1 | 11/1996 | |
| WO | WO96/34570 A1 | 11/1996 | |
| WO | WO96/34650 A1 | 11/1996 | |
| WO | WO96/34652 A1 | 11/1996 | |
| WO | WO96/34653 A1 | 11/1996 | |
| WO | WO96/36860 A2 | 11/1996 | |
| WO | WO96/39967 A1 | 12/1996 | |
| WO | WO97/15919 A1 | 5/1997 | |
| WO | WO97/17893 A1 | 5/1997 | |
| WO | WO97/17904 A1 | 5/1997 | |
| WO | WO97/25917 A1 | 7/1997 | |
| WO | WO97/25919 A1 | 7/1997 | |
| WO | WO97/32525 A1 | 9/1997 | |
| WO | WO97/36541 A1 | 10/1997 | |
| WO | WO97/40760 A1 | 11/1997 | |
| WO | WO97/42996 A1 | 11/1997 | |
| WO | WO98/18520 A2 | 5/1998 | |
| WO | WO98/19611 A1 | 5/1998 | |
| WO | WO98/26724 A1 | 6/1998 | |
| WO | WO98/28039 A2 | 7/1998 | |
| WO | WO98/38913 A1 | 9/1998 | |
| WO | WO99/02096 A1 | 1/1999 | |
| WO | WO99/56644 A1 | 11/1999 | |
| WO | WO99/56647 A1 | 11/1999 | |
| WO | WO99/56648 A1 | 11/1999 | |
| WO | WO99/56649 A1 | 11/1999 | |
| WO | WO00/78239 A2 | 12/2000 | |
| WO | WO02/060523 A2 | 8/2002 | |
| WO | WO03/041602 A2 | 5/2003 | |
| WO | WO03/089997 A2 | 10/2003 | |
| WO | WO2005/027765 A1 | 3/2005 | |
| WO | WO2005/027766 A1 | 3/2005 | |
| WO | WO2005/065562 A1 | 7/2005 | |
| WO | WO2005/065563 A1 | 7/2005 | |
| WO | WO2005/104972 A2 | 11/2005 | |
| WO | WO2006/017517 A2 | 2/2006 | |
| WO | WO2006/044794 A2 | 4/2006 | |
| WO | 2006052905 A2 | 5/2006 | |
| WO | 2007016123 A2 | 2/2007 | |
| WO | 2007024785 A2 | 3/2007 | |

OTHER PUBLICATIONS

"Werneth et al.; U.S. Appl. No. 12/116,753 entitled ""Ablation therapy system and method for treating continuous atrial fibrillation,"" filed May 7, 2008".

Sherman et. al. ; U.S. Appl. No. 12/117,596 entitled "RF energy delivery system and method, "filed May 8, 2008.

Oral et al.; U.S. Appl. No. 12/176,115 entitled "Atrial ablation catheter adapted for treatment of septal wall arrhythmogenic foci and method of use," filed Jul. 18, 2008.

Kunis et al.; U.S. Appl. No. 12/197,425 entitled "Atrial ablation catheter and method of use," filed Aug. 25, 2008.

Oral et al., "Catheter ablation for paroxysmal atrial fibrillation: segmental pulmonary vein ostial ablation versus left atrial ablation," Circulation, vol. 108, pp. 2355-2360.

Oral et al., "Segmental ostial ablation to isolate the pulmonary veins during atrial fibrillation: feasibility and mechanistic insights," Circulation, vol. 106, pp. 1256-1262.

Wittkampf et al., "Radiofrequency ablation with a cooled porous electrode catheter," (abstract) JACC, vol. 11, No. 2, pp. 17a, Feb. 1988.

Nademanee et al., "A new approach for catheter ablation of atrial fibrillation: mapping of the elecgrophysiologic substrate," JACC, vol. 43, No. 11, pp. 2044-2053 (2004).

* cited by examiner

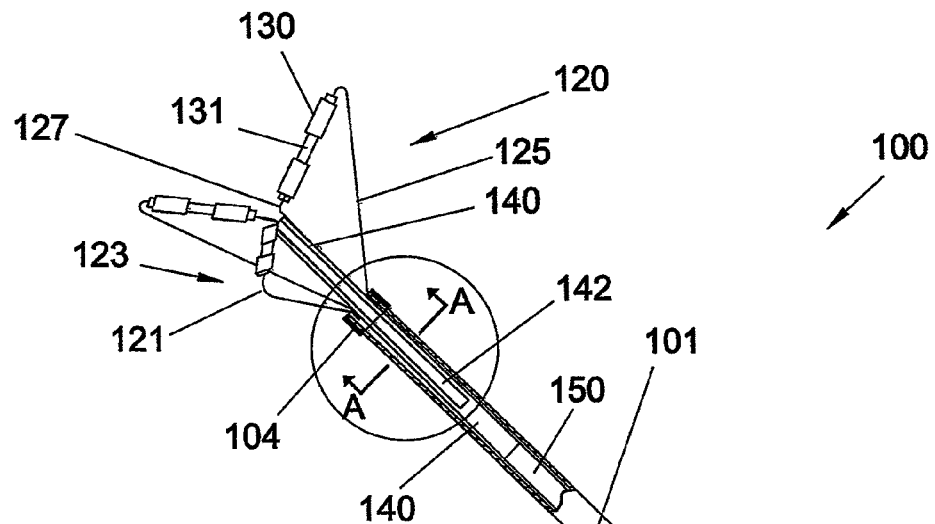
Fig. 6
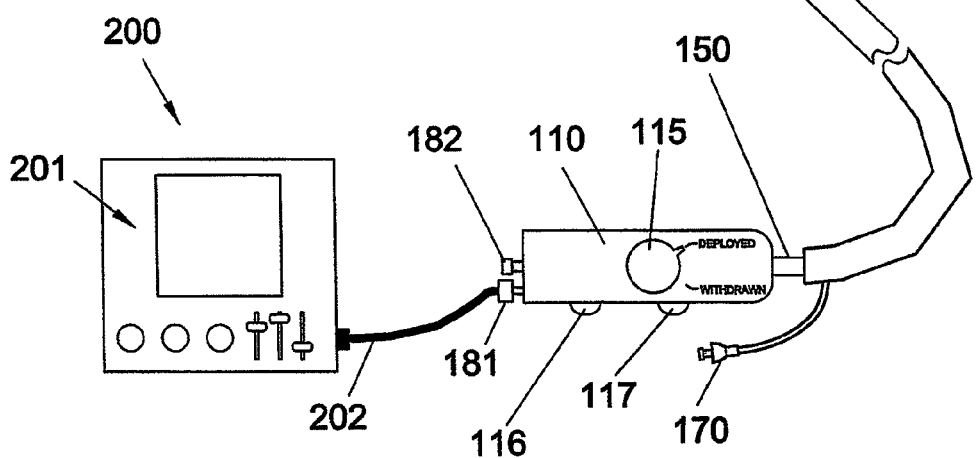
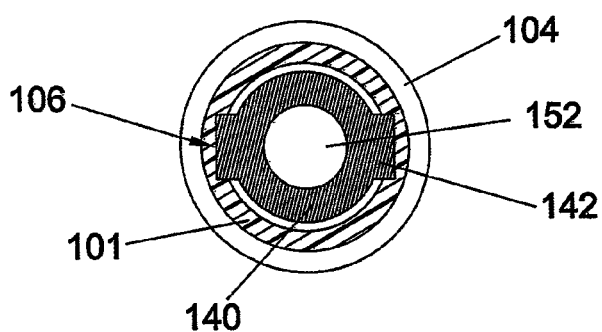
Fig. 6a

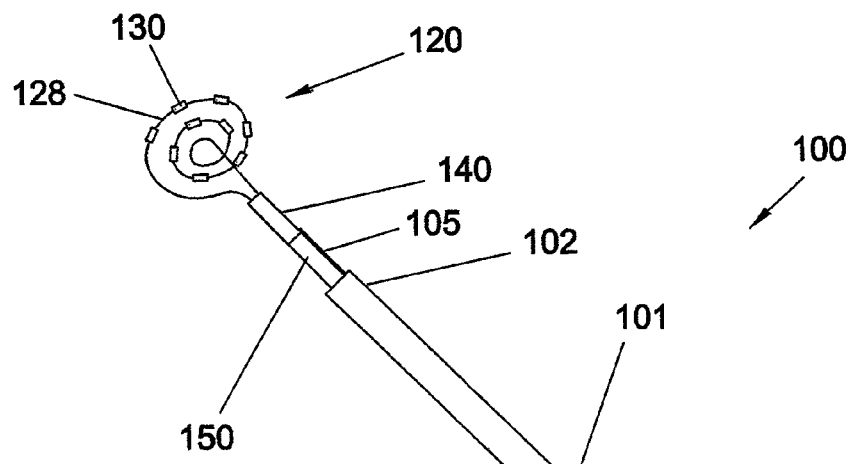
Fig. 7
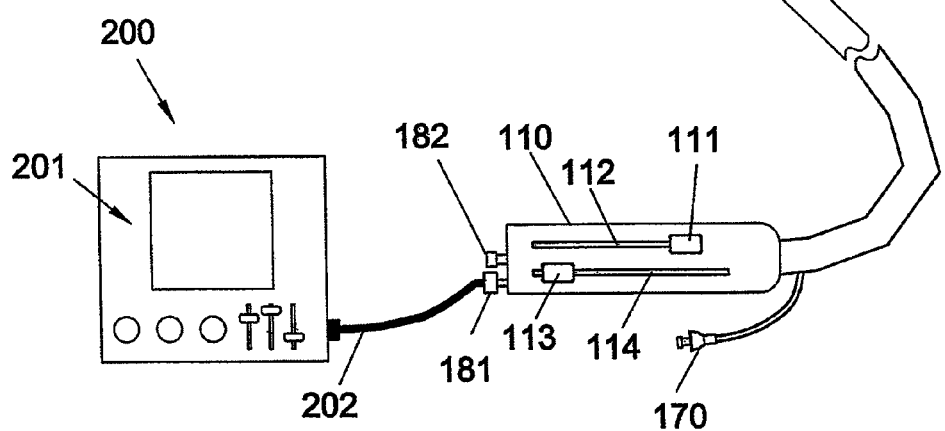
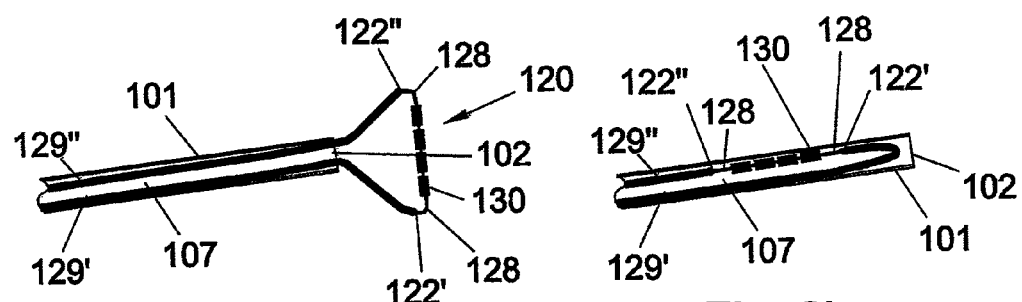
Fig. 8a                Fig. 8b

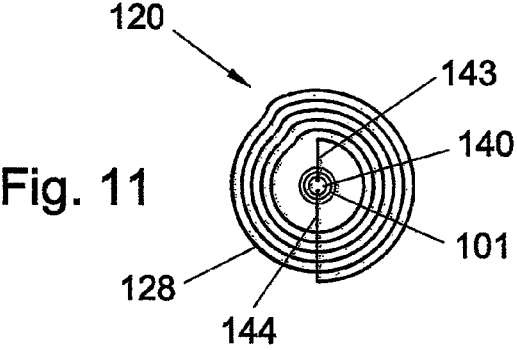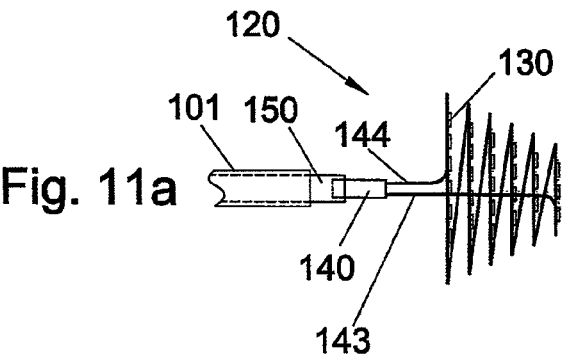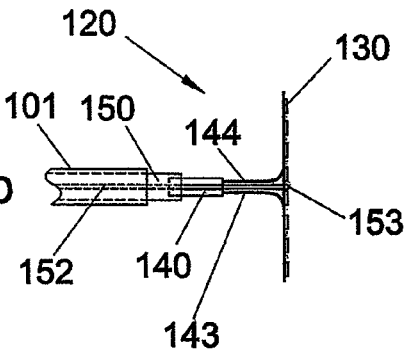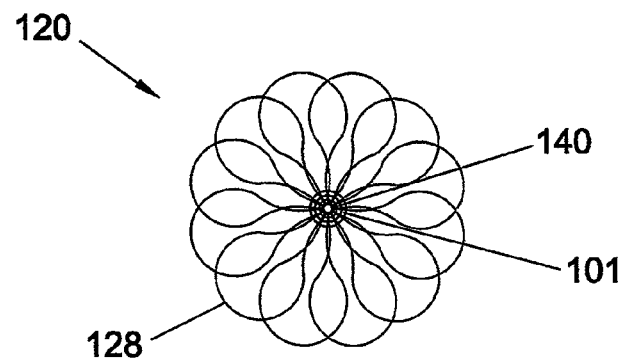
Fig. 12

ABLATION CATHETER

CROSS REFERENCE TO RELATED APPLICATIONS

This application is a continuation of U.S. patent application Ser. No. 11/179,333, filed Jul. 12, 2005 entitled "Ablation Catheter," which claims the benefit under 35 U.S.C. 119 of U.S. Patent Application No. 60/618,753 filed Oct. 14, 2004, entitled "Ablation Catheter".

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates generally to catheters and methods for performing targeted tissue ablation in a subject. In particular, the present invention provides devices comprising catheters having distal ends configured to treat two dimensional regions of target tissue, including deployable distal ends, and methods for treating conditions (e.g., cardiac arrhythmias) with these and similar devices.

BACKGROUND OF THE INVENTION

Tissue ablation is used in numerous medical procedures to treat a patient. Ablation can be performed to remove undesired tissue such as cancer cells. Ablation procedures may also involve the modification of the tissue without removal, such as to stop electrical propagation through the tissue in patients with an arrhythmia. Often the ablation is performed by passing energy, such as electrical energy, through one or more electrodes causing the tissue in contact with the electrodes to heats up to an ablative temperature. Ablation procedures can be performed on patients with atrial fibrillation by ablating tissue in the heart.

Mammalian organ function typically occurs through the transmission of electrical impulses from one tissue to another. A disturbance of such electrical transmission may lead to organ malfunction. One particular area where electrical impulse transmission is critical for proper organ function is in the heart. Normal sinus rhythm of the heart begins with the sinus node generating an electrical impulse that is propagated uniformly across the right and left atria to the atrioventricular node. Atrial contraction leads to the pumping of blood into the ventricles in a manner synchronous with the pulse.

Atrial fibrillation refers to a type of cardiac arrhythmia where there is disorganized electrical conduction in the atria causing rapid uncoordinated contractions that result in ineffective pumping of blood into the ventricle and a lack of synchrony. During atrial fibrillation, the atrioventricular node receives electrical impulses from numerous locations throughout the atria instead of only from the sinus node. This overwhelms the atrioventricular node into producing an irregular and rapid heartbeat. As a result, blood pools in the atria that increases a risk for blood clot formation. The major risk factors for atrial fibrillation include age, coronary artery disease, rheumatic heart disease, hypertension, diabetes, and thyrotoxicosis. Atrial fibrillation affects 7% of the population over age 65.

Atrial fibrillation treatment options are limited. Lifestyle change only assists individuals with lifestyle related atrial fibrillation. Medication therapy assists only in the management of atrial fibrillation symptoms, may present side effects more dangerous than atrial fibrillation, and fail to cure atrial fibrillation. Electrical cardioversion attempts to restore sinus rhythm but has a high recurrence rate. In addition, if there is a blood clot in the atria, cardioversion may cause the clot to leave the heart and travel to the brain or to some other part of the body, which may lead to stroke. What are needed are new methods for treating atrial fibrillation and other conditions involving disorganized electrical conduction.

Various ablation techniques have been proposed to treat atrial fibrillation, including the Cox-Maze procedure, linear ablation of various regions of the atrium, and circumferential ablation of pulmonary vein ostia. The Cox-Maze procedure and linear ablation procedures are tedious and time-consuming, taking several hours to accomplish. Pulmonary vein ostial ablation is proving to be difficult to do, and has lead to rapid stenosis and potential occlusion of the pulmonary veins. There is therefore a need for improved atrial ablation products and techniques.

BRIEF DESCRIPTION OF THE DRAWINGS

The accompanying drawings, which are incorporated in and constitute a part of this specification, illustrate various embodiments of the present invention, and, together with the description, serve to explain the principles of the invention. In the drawings:

FIG. 6 illustrates a perspective, partial cutaway view of an ablation catheter consistent with the present invention in which the carrier element has three carrier arms, the ablation catheter further including a handle for performing multiple functions.

FIG. 6*a* illustrates a sectional view of the distal end of the ablation catheter of FIG. 6.

FIG. 7 illustrates a perspective view of an ablation catheter consistent with the present invention in which the carrier element is in a spiral configuration.

FIGS. 8*a* and 8*b* are sectional views of the distal end of an ablation catheter consistent with the present invention in which the carrier assembly and control shaft are a continuous conduit. FIG. 8*a* illustrating the carrier assembly in a fully deployed condition and FIG. 8*b* illustrating the carrier assembly in a fully constrained condition.

FIG. 11 is an end view of a carrier assembly of an ablation catheter consistent with the present invention.

FIG. 11a is a side sectional view of the distal portion of the ablation catheter of FIG. 11 in which the carrier assembly lies in multiple planes when fully expanded.

FIG. 11b is a side sectional view of the distal portion of the ablation catheter of FIG. 11 in which the carrier assembly lies in a single plane when fully expanded.

FIG. 12 is an end view of the carrier assembly of an ablation catheter consistent with the present invention in which the carrier assembly consists of multiple wire segments each attached to a coupler.

DETAILED DESCRIPTION OF THE INVENTION

Figure 1:
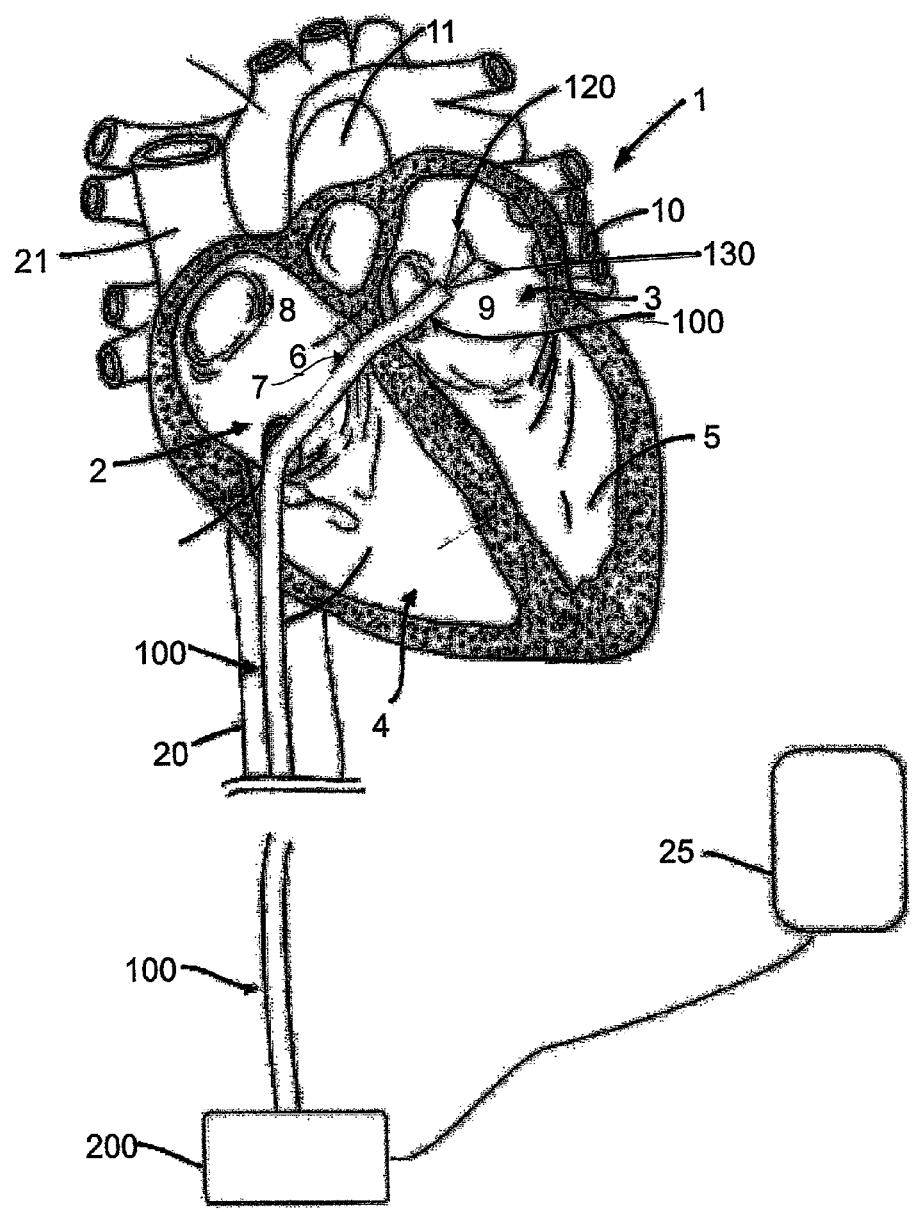
FIG. 1 illustrates the treatment to be accomplished with the devices and methods described below.

Reference will now be made in detail to the present embodiments of the invention, examples of which are illustrated in the accompanying drawings. Wherever possible, the same reference numbers will be used throughout the drawings to refer to the same or like parts.

The present invention provides catheters for performing targeted tissue ablation in a subject. In preferred embodiments, the catheters comprise a tubular body member having a proximal end and distal end and preferably a lumen extending therebetween. The catheter is preferably of the type used for performing intracardiac procedures, typically being introduced from the femoral vein in a patient's leg. The catheter is preferably introducable through a sheath and also preferably has a steerable tip that allows positioning of the distal portion such as when the distal end of the catheter is within a heart chamber. The catheters include ablation elements mounted on a carrier assembly. The carrier assembly is attached to a coupler, which in turn is connected to a control shaft that is coaxially disposed and slidingly received within the lumen of the tubular body member. The carrier assembly is deployable from the distal end of the tubular body member by advancing the control shaft, such as to engage one or more ablation elements against cardiac tissue, typically atrial wall tissue or other endocardial tissue. Retraction of the control shaft causes the carrier assembly to be constrained within the lumen of the tubular body member.

Arrays of ablation elements, preferably electrode arrays, may be configured in a wide variety of ways and patterns. In particular, the present invention provides devices with electrode arrays that provide electrical energy, such as radiofrequency (RF) energy, in monopolar (unipolar), bipolar or combined monopolar-bipolar fashion, as well as methods for treating conditions (e.g., atrial fibrillation, supra ventricular tachycardia, atrial tachycardia, ventricular tachycardia, ventricular fibrillation, and the like) with these devices. Alternative to or in combination with ablation elements that deliver electrical energy to tissue, other forms and types of energy can be delivered including but not limited to: sound energy such as acoustic energy and ultrasound energy; electromagnetic energy such as electrical, magnetic, microwave and radiofrequency energies; thermal energy such as heat and cryogenic energies; chemical energy such as energy generated by delivery of a drug; light energy such as infrared and visible light energies; mechanical and physical energy; radiation; and combinations thereof.

As described above, the normal functioning of the heart relies on proper electrical impulse generation and transmission. In certain heart diseases (e.g., atrial fibrillation) proper electrical generation and transmission are disrupted or are otherwise abnormal. In order to prevent improper impulse generation and transmission from causing an undesired condition, the ablation catheters of the present invention may be employed.

One current method of treating cardiac arrhythmias is with catheter ablation therapy. Physicians make use of catheters to gain access into interior regions of the body. Catheters with attached electrode arrays or other ablating devices are used to create lesions that disrupt electrical pathways in cardiac tissue. In the treatment of cardiac arrhythmias, a specific area of cardiac tissue having aberrant conductive pathways, such as atrial rotors, emitting or conducting erratic electrical impulses, is initially localized. A user (e.g., a physician) directs a catheter through a main vein or artery into the interior region of the heart that is to be treated. The ablating element is next placed near the targeted cardiac tissue that is to be ablated. The physician directs energy, provided by a source external to the patient, from one or more ablation elements to ablate the neighboring tissue and form a lesion. In general, the goal of catheter ablation therapy is to disrupt the electrical pathways in cardiac tissue to stop the emission of and/or prevent the propagation of erratic electric impulses, thereby curing the heart of the disorder. For treatment of atrial fibrillation, currently available methods and devices have shown only limited success and/or employ devices that are extremely difficult to use or otherwise impractical.

The ablation catheters of the present invention allow the generation of lesions of appropriate size and shape to treat conditions involving disorganized electrical conduction (e.g., atrial fibrillation). The ablation catheters of the present invention are also practical in terms of ease-of-use and limiting risk to the patient, as well as significantly reducing procedure times. The present invention addresses this need with, for example, spiral shaped and radial arm shaped (also called umbrella shaped) carrier assemblies whose ablation elements create spiral, radial, or other simple or complex shaped patterns of lesions in the endocardial surface of the atria by delivery of energy to tissue or other means. The lesions created by the ablation catheters are suitable for inhibiting the propagation of inappropriate electrical impulses in the heart for prevention of reentrant arrhythmias.

Definitions. To facilitate an understanding of the invention, a number of terms are defined below.

As used herein, the terms "subject" and "patient" refer to any animal, such as a mammal like livestock, pets, and preferably a human. Specific examples of "subjects" and "patients" include, but are not limited, to individuals requiring medical assistance, and in particular, requiring atrial fibrillation catheter ablation treatment.

As used herein, the terms "catheter ablation" or "ablation procedures" or "ablation therapy," and like terms, refer to what is generally known as tissue destruction procedures. Ablation is often used in treating several medical conditions, including abnormal heart rhythms. It can be performed both surgically and non-surgically. Non-surgical ablation is typically performed in a special lab called the electrophysiology (EP) laboratory. During this non-surgical procedure a catheter is inserted into the heart using fluoroscopy for visualization, and then an energy delivery apparatus is used to direct energy to the heart muscle. This energy either "disconnects" or "isolates" the pathway of the abnormal rhythm (depending on the type of ablation). It can also be used to disconnect the conductive pathway between the upper chambers (atria) and the lower chambers (ventricles) of the heart. For individuals requiring heart surgery, ablation can be performed during coronary artery bypass or valve surgery.

As used herein, the term "ablation element" refers to an energy delivery element, such as an electrode for delivering electrical energy. Ablation elements can be configured to deliver multiple types of energy, such as ultrasound energy and cryogenic energy, either simultaneously or serially. Electrodes can be constructed of a conductive plate, wire coil, or other means of conducting electrical energy through contacting tissue. In monopolar energy delivery, the energy is conducted from the electrode, through the tissue to a ground pad, such as a conductive pad attached to the back of the patient. The high concentration of energy at the electrode site causes localized tissue ablation. In bipolar energy delivery, the energy is conducted from a first electrode to one or more separate electrodes, relatively local to the first electrode, through the tissue between the associated electrodes. Bipolar energy delivery results in more precise, shallow lesions while monopolar delivery results in deeper lesions. Both monopolar and bipolar delivery provide advantages, and the combination of their use is a preferred embodiment of this application. Energy can also be delivered using pulse width modulated drive signals, well known to those of skill in the art. Energy can also be delivered in a closed loop fashion, such as a system with temperature feedback wherein the temperature modifies the type, frequency and or magnitude of the energy delivered.

As used herein, the term "carrier assembly" refers to a flexible carrier, on which one or more ablation elements are disposed. Carrier assemblies are not limited to any particular size, or shape, and can be configured to be constrained within an appropriately sized lumen.

As used herein, the term "spiral tip" refers to a carrier assembly configured in its fully expanded state into the shape of a spiral. The spiral tip is not limited in the number of spirals it may contain. Examples include, but are not limited to, a wire tip body with one spiral, two spirals, ten spirals, and a half of a spiral. The spirals can lie in a relatively single plane, or in multiple planes. A spiral tip may be configured for energy delivery during an ablation procedure.

As used herein the term "umbrella tip" refers to a carrier assembly with a geometric center which lies at a point along the axis of the distal portion of the tubular body member, with one or more bendable or hinged carrier arms extending from the geometric center, in an umbrella configuration. Each carrier arm may include one or more ablation elements. Each carrier arm of an umbrella tip includes a proximal arm segment and a distal arm segment, the distal arm segment more distal than the proximal arm segment when the carrier assembly is in a fully expanded condition. One or more additional carrier arms can be included which include no ablation elements, such as carrier arms used to provide support or cause a particular deflection. An umbrella tip body is not limited to any particular size. An umbrella tip may be configured for energy delivery during an ablation procedure.

As used herein, the term "lesion," or "ablation lesion," and like terms, refers to tissue that has received ablation therapy. Examples include, but are not limited to, scars, scabs, dead tissue, burned tissue and tissue with conductive pathways that have been made highly resistive or disconnected.

As used herein, the term "spiral lesion" refers to an ablation lesion delivered through a spiral tip ablation catheter. Examples include, but are not limited to, lesions in the shape of a wide spiral, and a narrow spiral, a continuous spiral and a discontinuous spiral.

As used herein, the term "umbrella lesion" or "radial lesion," and like terms, refers to an ablation lesion delivered through an umbrella tip ablation catheter. Examples include, but are not limited to, lesions with five equilateral prongs extending from center point, lesions with four equilateral prongs extending from center point, lesions with three equilateral prongs extending from center point, and lesions with three to five non-equilateral prongs extending from center point.

As used herein, the term "coupler" refers to an element that connects the carrier assembly to the control shaft. Multiple shafts, or ends of the carrier assembly may connect to the coupler. Multiple carrier arms can have one or more of their ends attached to the coupler. The coupler may include antirotation means that work in combination with mating means in the tubular body member. Couplers may be constructed of one or more materials such as polyurethane, steel, titanium, and polyethylene.

As used herein, the term "carrier arm" refers to a wire-like shaft capable of interfacing with electrodes and the coupler. A carrier arm is not limited to any size or measurement. Examples include, but are not limited to: stainless steel shafts; Nitinol shafts; titanium shafts; polyurethane shafts; nylon shafts; and steel shafts. Carrier arms can be entirely flexible, or may include flexible and rigid segments.

As used herein, the term "carrier arm bend point" refers to a joint (e.g., junction, flexion point) located on a carrier arm. The degree of flexion for a carrier arm bend point may range from 0 to 360 degrees. The bend portion can be manufactured such what when the carrier assembly is fully expanded the bend point is positioned in a relatively straight portion, a curved portion, or in a discrete transition from a first direction to a second transition, such as a 45 degree bend transition. The bend portion can include one or more flexing means such as a spring, a reduced diameter segment, or a segment of increased flexibility.

The present invention provides structures that embody aspects of the ablation catheter. The present invention also provides tissue ablation systems and methods for using such ablation systems. The illustrated and preferred embodiments discuss these structures and techniques in the context of catheter-based cardiac ablation. These structures, systems, and techniques are well suited for use in the field of cardiac ablation.

However, it should be appreciated that the invention is applicable for use in other tissue ablation applications such as tumor ablation procedures. For example, the various aspects of the invention have application in procedures for ablating tissue in the prostate, brain, gall bladder, uterus, and other regions of the body, preferably regions with an accessible wall or flat tissue surface, using systems that are not necessarily catheter-based.

The multifunctional catheters of the present invention have advantages over previous prior art devices. FIGS. 1-12 show various preferred embodiments of the multifunctional catheters of the present invention. The present invention is not limited to these particular configurations.

FIG. 1 illustrates the treatment to be accomplished with the devices and methods described herebelow. FIG. 1 shows a cutaway view of the human heart 1 showing the major structures of the heart including the right atrium 2, the left atrium 3, the right ventricle 4, and the left ventricle 5. The atrial septum 6 separates the left and right atria. The fossa ovalis 7 is a small depression in the atrial septum that may be used as an access pathway to the left atrium from the right atrium. The fossa ovalis 7 can be punctured, and easily reseals and heals after procedure completion. In a patient suffering from atrial fibrillation, aberrant electrically conducive tissue may be found in the atrial walls 8 and 9, as well as in the pulmonary veins 10 and the pulmonary arteries 11. Ablation of these areas, referred to arrhythmogenic foci (also referred to as drivers or rotors), is an effective treatment for atrial fibrillation. Though circumferential ablation of the pulmonary vein usually cures the arrhythmia that originates in the pulmonary veins, it may result in eventual stenosis of these pulmonary veins, a very undesirable condition. The catheters of the present invention provide means of creating lesions remote from these pulmonary veins and their ostia while easily being deployed to ablate the driver and rotor tissue.

To accomplish this, catheter 100 is inserted into the right atrium 2, preferably through the inferior vena cava 20, as shown in the illustration, or through the superior vena cava 21. Catheter 100 may include an integral sheath, such as a tip deflecting sheath, or may work in combination with a separate sheath. When passing into the left atrium, the catheter passes through or penetrates the fossa ovalis 7, such as over a guide wire placed by a trans-septal puncture device. The catheter 100 carries a structure carrying multiple ablation elements such as RF electrodes, carrier assembly 120, into the left atrium. Carrier assembly 120 is adapted to be deformable such that pressing carrier assembly into left atrial wall 9 will cause one or more, and preferably all of electrodes 130 to make contact with tissue to be analyzed and/or ablated. Each of the electrodes 130 is attached via connecting wires to an energy delivery apparatus, RF delivery unit 200 which is also attached to patch electrode 25, preferably a conductive pad attached to the back of the patient.

RF delivery unit 200 is configured to delivery RF energy in monopolar, bipolar or combination monopolar-bipolar energy delivery modes. In a preferred embodiment, monopolar energy delivery is followed by bipolar energy delivery, which is then followed a period without energy delivery, such as a sequence in which the three steps are have equal durations. In another preferred embodiment, RF delivery unit 200 is configured to also provide electrical mapping of the tissue that is contacted by one or more electrodes integral to carrier assembly 120. Electrodes 130 can also be configured to be mapping electrodes and/or additional electrodes can be integral to carrier assembly 120 to provide a mapping function. Carrier assembly 120 is configured to be engaged over an endocardial surface to map and/or ablate tissue on the surface. RF energy is delivered after a proper location of the electrodes 130 is confirmed with a mapping procedure. If the position is determined to be inadequate, carrier assembly 120 is repositioned through various manipulations at the proximal end of the ablation catheter 100. In another preferred embodiment, RF delivery unit 200 is configured to delivery both RF energy and ultrasound energy the identical or different electrodes 130. In another preferred embodiment, RF delivery unit 200 is configured to accept a signal from one or more sensors integral to ablation catheter 100, not shown, such that the energy delivered can be modified via an algorithm which processes the information received from the one or more sensors.

Figure 2:
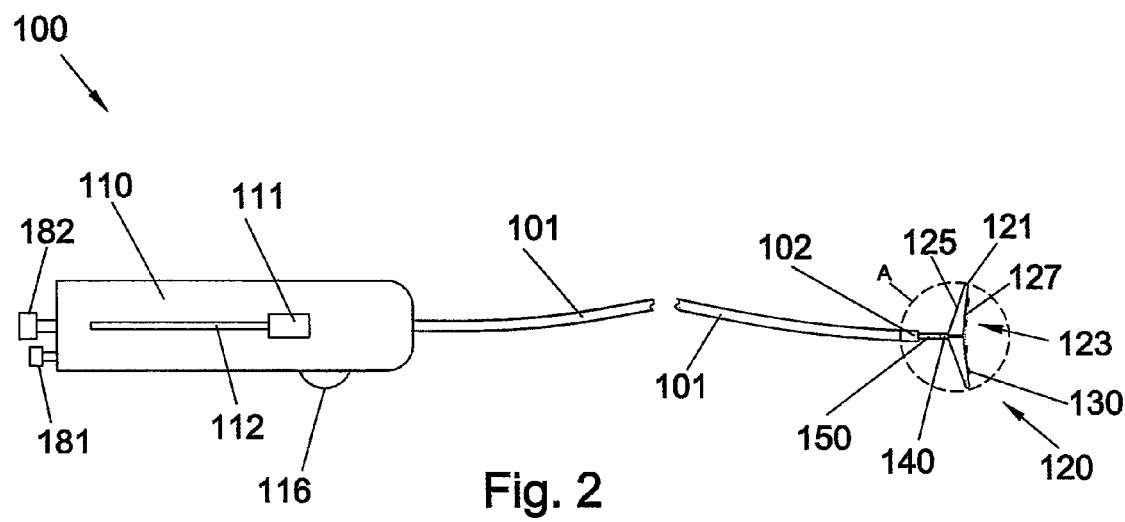
FIG. 2 illustrates a side view of an ablation catheter consistent with the present invention.

Referring now to FIG. 2, a preferred embodiment of ablation catheter 100 is illustrated. Ablation catheter 100 includes a tubular body member which is an elongated, flexible, hollow tube, catheter shaft 101, that connects at its proximal end to handle 110. The material used for the construction of the catheter shaft 101 and each component which resides or is configured to be inserted through a lumen integral to catheter shaft 101, are selected to provide the suitable flexibility, column strength and steerability to allow percutaneous introduction of ablation catheter 100 to various body locations including the left or right atrium of the heart. Catheter shaft 101 and other tubular conduits of ablation catheter 100 are constructed of materials such as Pebax™; polyimide; polyurethane; silicone; nylon; polyvinyl chloride (PVC); polyester; and combinations thereof. These types of conduits may be constructed of an outer layer, an inner layer and a braid residing therebetween. The braid may be constructed of various materials including stainless steel; Nitinol; monofilament fiber; a polymer; and combinations thereof.

Control shaft 150 extends from the proximal end to distal end 102 of catheter shaft 101 and resides in a lumen therebetween. Control shaft 150 is also constructed of material to provide suitable flexibility and column strength to be percutaneously introduced into the patient as well as perform other functions such as the advancement and contraction of carrier assembly 120. Applicable materials for control shaft 150 are Nitinol™; stainless steel; titanium; gold; platinum; copper; a polymer; a polymer embedded with conductive material; an elastomer; a plastic; and combinations thereof. In a preferred embodiment, control shaft 150 is constructed of both stainless steel and Nitinol. In another preferred embodiment, control shaft 150 is selected from the group consisting of: a monofilament fiber; a spring coil; a wire; and combinations thereof. In another preferred embodiment, control shaft 150 has a guidewire construction such as a core with a tightly coiled wire sheath, the sheath surrounding a substantial length of the core. In another preferred embodiment, the control shaft 150 includes a lumen from its proximal end and its distal end 102 such as to permit over-the-wire introduction via that lumen.

Coupler 140, located at the distal end 102 of control shaft 150 connects control shaft 150 to carrier assembly 120. Carrier assembly 120 is a flexible filamentous assembly that includes at least one ablation element, such as electrode 130, to deliver energy to tissue. Carrier assembly 120 includes one or more carrier arms 123, each of which has a proximal arm segment 125 and a distal arm segment 127, which are connected by a resiliently flexible segment, carrier arm bend portion 121. Bend portion 121 may include various elements to assist in bending such as a spring; a hinge; a reduced diameter segment; a bend created during a heat treatment of a wire such as the "training" of a Nitinol wire; and combinations thereof. Bend point 121 provides means for rotatably joining the distal arm segment 127 to the proximal arm segment 125. Carrier arms 123 are preferably constructed of a wire, such as a ribbon wire, and may have segments with different levels of flexibility. Bend point 121 may comprises two or more wires bonded together with a joint. Carrier arms 123 may include no ablation elements, such as a carrier arm 123 to provide support only. Carrier arms 123 may also include mapping electrodes, thermal sensors or other sensors, with or without the inclusion of ablation elements. In a preferred embodiment, each carrier arm 123 includes at least one ablation element.

Figure 3:
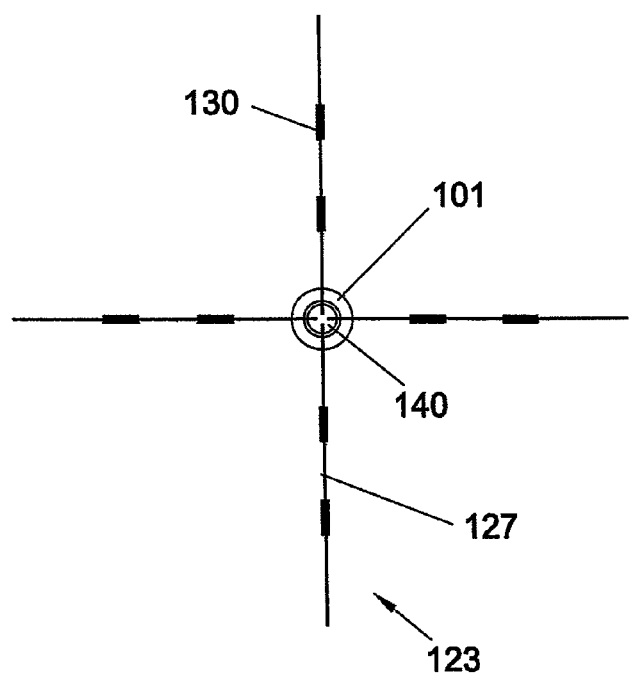
FIG. 3 illustrates an end view of the distal portion of the ablation catheter of FIG. 2.
Figure 4:
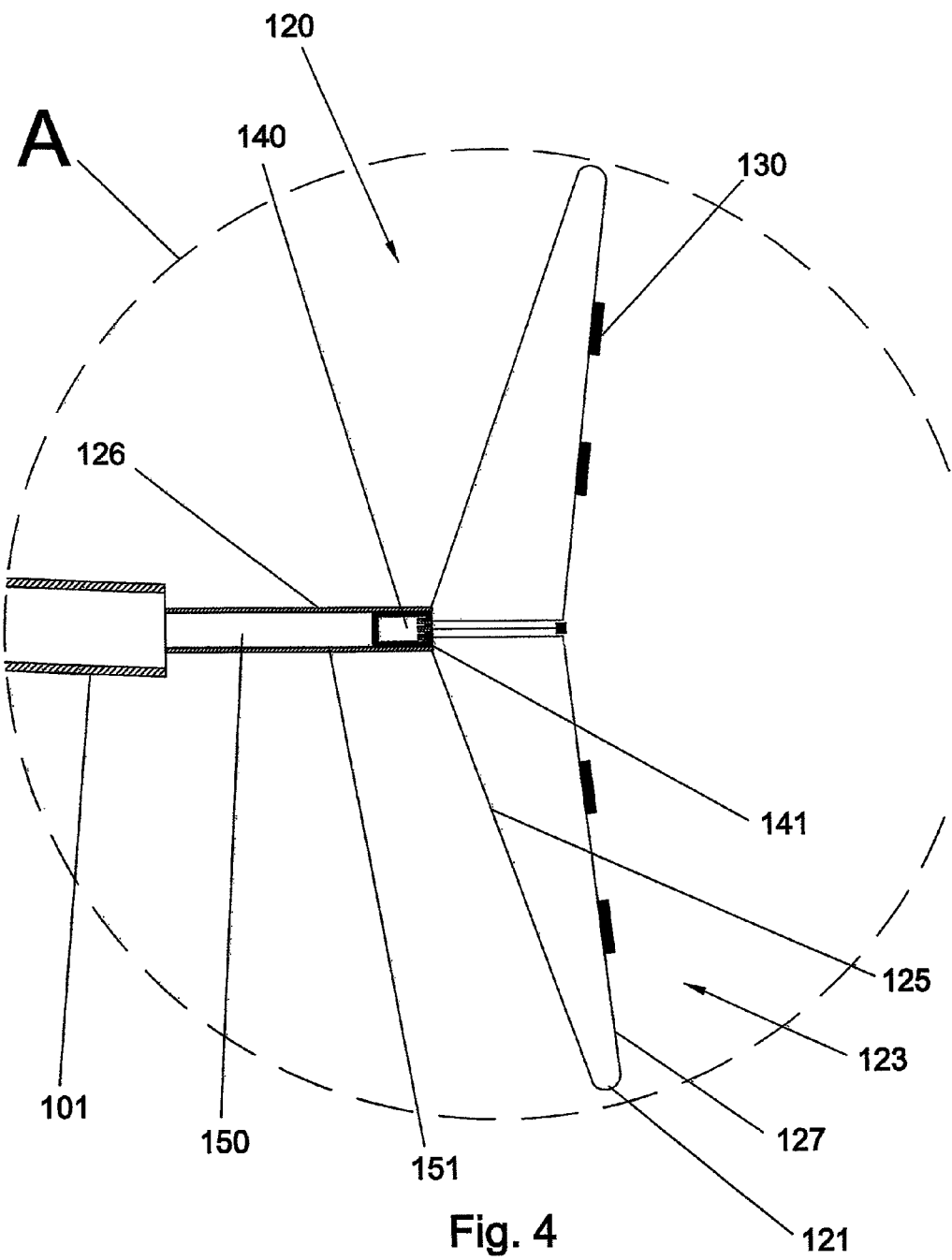
FIG. 4 illustrates an enlarged sectional view of the distal portion of the ablation catheter of FIG. 2
Figure 5:
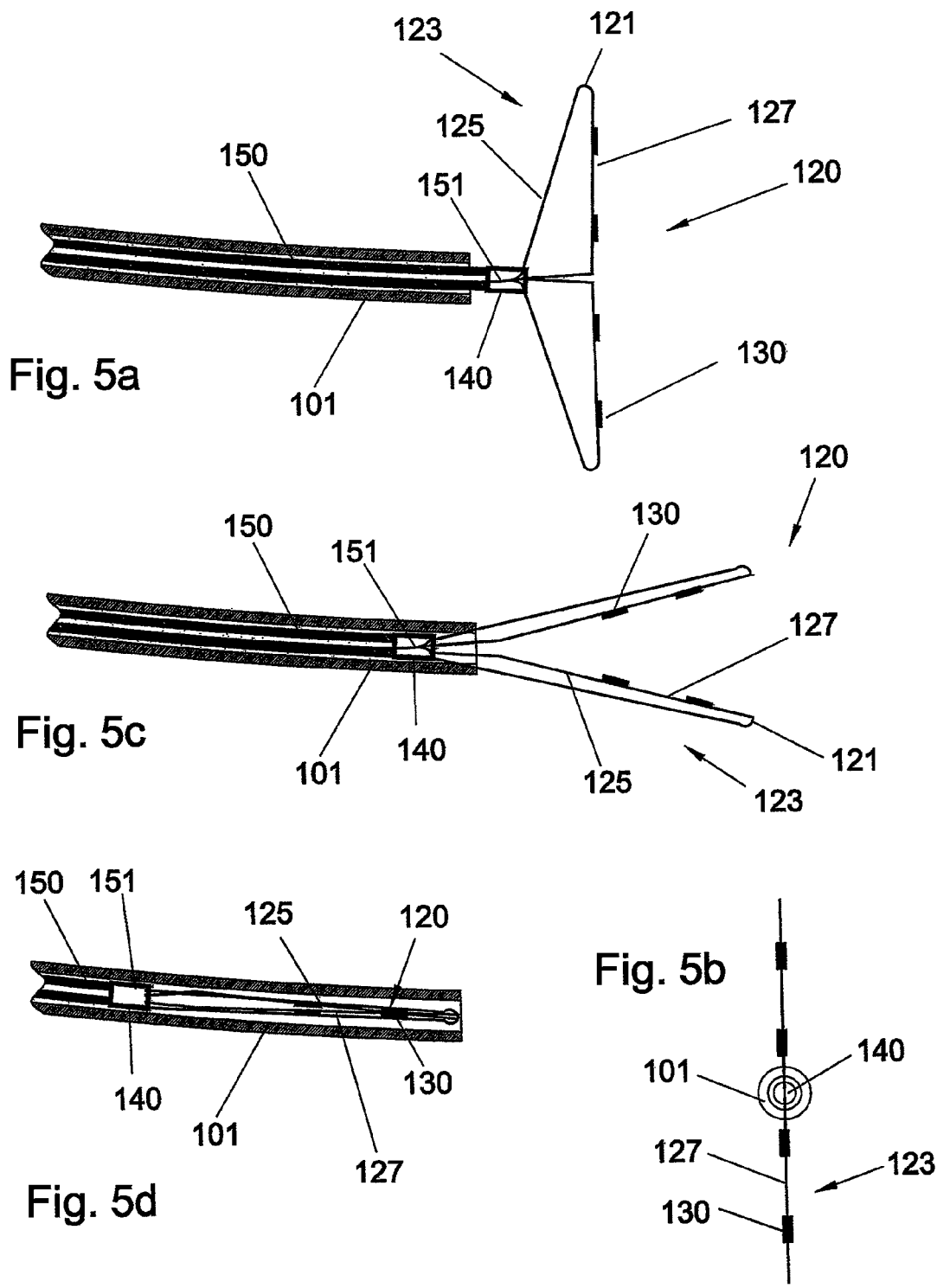
FIGS. 5*a*-5*d* illustrate a sectional view of the distal portion of the ablation catheter of FIG. 2 demonstrating a series of deployments of the carrier assembly in a fully deployed, partially constrained and fully constrained condition, respectively.

Carrier assembly 120 can be configured to assume various geometries when in its expanded condition, such as the umbrella configuration of FIG. 2 through 4. Carrier assembly 120, coupler 140 and control shaft 150 are configured such that control shaft 150 can be retracted to constrain carrier assembly 120 within a lumen of catheter shaft 101 and advancement of control shaft 150 causes carrier assembly 120 to advance beyond distal end 102 of control shaft 101 thus allowing carrier assembly 120 to deploy to its fully expanded condition. Coupler 140 is preferably more rigid than control shaft 150. Control shaft 150 extends proximally to a location inside handle 110 where it is operably connected to knob 111 that slides in slot 112. Alternative to sliding knob 111 is a rotating knob or a mechanical or electromechanical linear actuator, not shown. Sliding knob 111 is configured such that an operator of the system can with minimal effort advance and deploy carrier assembly 120 to its distal position where it is fully deployed for engagement with tissue, as well as retract and constrain carrier assembly within a lumen at the distal end 102 of catheter shaft 101. One or more knobs can work in conjunction with a cam assembly, or a series of gears, both not shown, such that motion or force can be multiplied with the resultant mechanical advantage.

Each electrode 130 of carrier assembly 120 of ablation catheter 100 is connected to one or more wires, not shown but preferably extending from each electrode 130 of the distal arm segment 127, running parallel with the segment toward the axis of distal end 102 of the catheter shaft 101, then traveling proximally toward coupler 140 and then through catheter shaft 101 to handle 110. The wires may pass through coupler 140, along side coupler 140, or may be electrically connected to coupler 140 such that these wires connect to wires on the proximal end of coupler 140. The wires may be within a lumen internal to control shaft 150, a space between control shaft 150 and catheter shaft 101, and a separate lumen of catheter shaft 101. The wires are looped within handle 110 to provide the distension necessary for the resilient deployment of carrier assembly 120 as illustrated in FIG. 2.

The electrode 130 wires provide a drive signal and a ground signal, or two or more alternating drive signals to each electrode 130. Electrodes 130 can be wired independently, such that each electrode 130 can deliver energy independent of any other electrode, or two or more electrodes can be connected in parallel or serial fashion. In a preferred embodiment, ablation catheter 100 and an energy delivery apparatus can be configured to drive two ablation elements, such as electrodes 130, independently or simultaneously. Handle 110 includes RF attachment port 181 which can be connected to a separate energy delivery apparatus such as an RF delivery apparatus. Mapping port 182 is also included, which can be used to connect to a mapping device to assist in determining and/or confirming the proper ablation location. Handle 110 further includes button 116, which is connected to switch means, not shown, for starting and/or stopping the delivery of energy to one or more of electrodes 130. In an alternative embodiment, an energy delivery apparatus is integrated into handle 110 such that a separate apparatus and port 181 are not needed. In this configuration, handle 110 may include a plug, not shown, for attachment to a power supply or wall outlet. In another alternative embodiment, handle 110 includes an audible transducer, such as an audible transducer that is activated when energy is being delivered to tissue, or an alarm condition has been entered. In another alternative embodiment, handle 110 includes a power supply, such as a battery or rechargeable battery, both not shown. In another alternative embodiment, ablation catheter 100 includes one or more elements requiring power such as from an integrated battery, these elements selected from the group consisting of: an integral a light such as an LED; a display such as a liquid crystal display or touch screen display; an audible transducer; a tactile transducer such as a vibration transducer which readily alerts anyone holding the device; a relay such as a relay which disconnects power to one or more ablation elements; mapping circuitry embedded in one or more components of ablation catheter 100, or electrode 130; and combinations thereof.

Referring now to FIG. 3, an end view of the distal end of the catheter of FIG. 2 is illustrated, showing the umbrella tip configuration. Four carrier arms 123 extend radially out from the central axis of catheter shaft 101, the arms positioned in a symmetric configuration with equal angles (ninety degrees in a four arm configuration) between each arm. In alternative embodiments, three or more arms can be separated by different angles. The four carrier arms 123 are connected to coupler 140 which is concentric with the axis of catheter shaft 101 and connected to control shaft 150, not shown. Each arm is shown with two electrodes 130 mounted to distal arm segment 127, preferably 1-4 mm in length and distributed in a radial pattern covering a range from 1 cm$^3$ to 12 cm$^3$. In a preferred embodiment, a first electrode is a different length than a second electrode.

Referring now to FIG. 4, an enlarged portion of the catheter of FIG. 2 at circle "A" is illustrated. Control shaft 150, which exits the distal end of catheter shaft 101, is connected to coupler 140. Carrier assembly 120 includes carrier arms 123, each of which includes proximal arm segment 125 and distal arm segment 127. One end of distal arm segment 127 is attached to coupler 140 with glue 141, near to the central axis of catheter shaft 101. In an alternative embodiment, the connection is made with a press fit or crimp. The other end of distal arm segment 127 transitions to proximal arm segment 125 through bend point 121. The other end of proximal arm segment 125 attaches to the distal end of control shaft 140 such as with glue, a circumferential band, or other attachment means at arm fixation portion 126.

Electrodes 130 are mounted to distal arm segment 127 of carrier arms 123. These electrodes can consist of wire coils; conductive plates; semiconductor plates; and combinations thereof. Each electrode is connected to one or more wires, each wire traveling from the electrode inward toward the axis of catheter shaft axis, and then proximal toward the end of control shaft 150. The wires are joined in a bundle, wire bundle 151 which travels along side control shaft 150. Wire bundle 151 may be glued or banded to control shaft 150 to avoid binding. In an alternative embodiment, wire bundle 151 travels internal to control shaft 150.

Carrier arm 123 includes proximal arm segment 125 and distal arm segment 127, carrier arm bend point 121. In the configuration of FIGS. 2 through 4, each proximal arm segment 125 resiliently bends radially outwardly from coupler 140, while each distal arm segment 127 bends radially inwardly from the bend point 121 toward the longitudinally axis of catheter shaft 101. The distal arm segments 127 are shown to also tend proximally, and to establish an acute angle with the proximal arm segment 125 from which it extends, and the angle is small such that the distal end of the distal arm segment 127 is proximal to the carrier arm bend point 121. In an alternative embodiment, the distal arm segments 127 are configured to tend distally, and to establish an obtuse angle with proximal arm segment 125. Proximal arm segment 125 and distal arm segment 127 are preferably Nitinol wires, such as a continuous flat wire that also includes bend point 121. The Nitinol wires can be trained to be flexible, but resiliently biases in a pre-determined shape. Wires are preferably of a non-circular cross-section such as an ova, rectangle, trapezoid or parallelepiped. The cross-section may vary along its length, and may be configured to cause preferential bending at a specific location and/or in a specific direction. In an alternative embodiment, proximal arm segment 125, distal arm segment 127 and/or bend point 121 are comprised of a non-metallic material such as a plastic, a monofilament flexible fiber or other non-metallic material. In a preferred embodiment, carrier assembly 120 is constructed such that it is more flexible than control shaft 150. In another preferred embodiment, carrier assembly 120 includes one or more wire segments, such as ribbon wire. In another preferred embodiment, carrier assembly 120 includes flat Nitinol wires.

Referring now to FIGS. 5a through 5d which illustrate the distal end of an ablation catheter of the current invention in various deployment conditions, specifically where carrier assembly 120 is in a fully deployed, partially constrained and fully constrained condition. Referring to FIG. 5a, carrier assembly 120 is shown with two carrier arms 123 with integral electrodes 130 aligned to form a linear lesion. The distal arm segments 127 are also aligned such as when the control shaft 150 is advanced pressing carrier assembly 120 against tissue. Carrier assembly 120, when deployed and flattened against a surface such as an endocardial surface, is preferably about 15 to 30 mm in diameter (to the outer extent of the carrier arm), with each distal arm segment 127 being about 7 to 15 mm long. The wire width of carrier assembly 120 shafts are preferably about 0.26 mm, and the distal face of the electrodes is preferably about 1 to 2 mm wide, and 2 to 3 mm long. Carrier assembly 120 is shown with two carrier arms 123, however any number can be used, and each arm can carry one or more electrodes, or be void of electrodes. Bipolar RF energy may be applied pairs of the electrodes, including an electrode near the distal portion of the ablation catheter but not integral to the carrier assembly, or monopolar energy may be applied to any of the electrodes 130, the energy grounded to a surface electrode or a return electrode located proximally on the catheter body. FIG. 5*b* shows an end view of the catheter of FIG. 5*a* in the same deployment condition. FIG. 5*b* depicts the two carrier arms 123 and the linear arrangement of electrodes 130. FIG. 5*c* shows a condition in which carrier assembly 120 is partially constrained, such as when control shaft 140 is retracted and/or catheter shaft 101 is advanced. Coupler 140 is shown completely within the lumen of catheter shaft 101, and an end of proximal arm segment 125 and an end of distal arm segment 127 is also within the lumen such that the other ends of proximal arm segment 125 and distal arm segment 127 are rotated inward toward the central axis of catheter shaft 101. FIG. 5*d* shows the carrier assembly in a completely constrained condition, such as when control shaft 140 is further retracted and/or catheter shaft 101 is further advanced. Now both ends of proximal arm segments 125 and distal arm segments 127 are constrained within the lumen of catheter shaft 101. The lumen of catheter shaft 101 and electrodes 130 are sized and shaped to allow carrier assembly 120 to be constrained within the lumen but permit easy advancement and retraction. In a preferred embodiment, control shaft 150, coupler 140 and carrier assembly 120 can be fully removed from catheter shaft 101, allowing reinsertion of an assembly with a different configuration of control shaft 150, coupler 140 and/or carrier assembly 120.

Referring now to FIGS. 6 and 6*a*, another preferred embodiment of ablation catheter 100 and ablation system of the present invention is illustrated. Catheter 100 includes carrier assembly 120 configured in another umbrella tip configuration. Carrier assembly 120 includes three carrier arms 123, each of which includes two electrodes 130. In an alternative embodiment, different patterns of electrodes are employed, and one or more arms may be void of electrodes. Referring back to FIG. 6, carrier arms 123 extend radially out from the central axis of the distal end of catheter shaft 101. Each carrier arm 123 includes proximal arm segment 125 and distal arm segment 127, these segments connected at a bendable joint, bend point 121. In a preferred embodiment, proximal arm segment 125 and distal arm segment 127 and bend point 121 are a continuous resiliently flexible wire, such as a "trained" Nitinol wire which creates the umbrella tip. Each electrode 130 is mounted to an insulator, insulating band 131 such that the electrode is electrically isolated from the wire segments of carrier assembly 120. Each electrode 130 is connected to wires which extend along shafts of carrier assembly 120, toward a lumen of catheter shaft 101, and proximally to handle 110. These wires, not shown but described in detail hereabove, include insulation to electrically isolate one wire from another. One end of each distal arm segment 127 is attached to a cylinder, coupler 140, which is sized to be slidably received within a lumen of catheter shaft 101.

Referring again to FIGS. 6 and 6*a*, coupler 140 can be flexible or rigid, and may contain both rigid and flexible portions along its length. Coupler 140 may provide electrical connection means to connect wires extending from the handle to wires from carrier assembly 120 electrodes. The ends of the distal arm segments 127 and the ends of the proximal arm segments 125 can be attached to the outside of coupler 140, the inside of coupler 140 or both. Coupler 140 includes along its outer surface, a projection, projection 142, which has a cross section profile which mates with a recess, groove 106 of catheter shaft 101 which prevents undesired rotation of carrier assembly 120. In an alternative embodiment, catheter shaft 101 includes a projection, and coupler 140 includes a groove to accomplish a similar prevention of rotation. In another alternative embodiment, control shaft 150 additionally or alternatively includes a projection or other means to mate with catheter shaft 101 to prevent undesired rotation of carrier assembly 120. As depicted in FIG. 6*a*, control shaft 140 includes a thru lumen, lumen 152, such that ablation catheter 101 can be inserted over a guidewire (guidewire exit on handle 110 not shown). Additionally or alternatively, lumen 150 may include one or more wires or other filamentous conduits extending from proximal handle 110 a point more distal.

Control shaft 150 is mechanically attached to coupler 140. Control shaft 150 extends proximally to handle 110 and is operably connected to knob 115 such that rotation of knob 115 from a deployed position to a withdrawn position causes carrier assembly 120 to be constrained within a lumen of catheter shaft 101, and rotation of knob 115 from a withdrawn position to a deployed position causes carrier assembly 120 to extend beyond the distal end of catheter shaft 101 to be in an expanded condition. In a preferred embodiment, knob 115 is operably connected to control shaft 150 via a cam, or set of gears, not shown, to provide a mechanical advantage in the distance traveled by control shaft 150.

Catheter shaft 101 is preferably part of a steerable sheath, steering mechanism not shown, and includes flush port 170, which is configured to be attachable to a flushing syringe, used to flush blood and other debris or contaminants from the lumen of an empty catheter shaft 101 (wherein control shaft 150, coupler 140 and carrier assembly 120 have been removed) or for flushing the space between control shaft 150 and the inner wall of catheter shaft 101. Catheter shaft 101 is not connected to handle 110, such that handle 110 can be withdrawn, removing control shaft 150, coupler 140 and carrier assembly 120 from catheter shaft 101. This configuration is useful when these components are provided in a kit form, including combinations of different versions of these components, the different combinations made available to treat multiple patients, or a single patient requiring multiple electrode patterns. A preferred example of a kit would include the catheter shaft 101 and flush port 170 of FIG. 6 acting as a sheath; kitted with handle 110, control shaft 150, coupler 140 and umbrella tipped carrier assembly 120 of FIG. 6 as well as handle 110, control shaft 150, coupler 140 and spiral tipped carrier assembly 120 of FIG. 7.

Also depicted in FIG. 6 is a system of the present invention, including in addition to ablation catheter 100, RF delivery unit 200, a energy delivery apparatus of the present invention which connects to handle 110 with a multi-conductor cable 202 attached to RF attachment port 181. RF delivery unit 200 includes user interface 201, such as a user interface including data input devices like touch screens, buttons, switches, keypads, magnetic readers and other input devices; and also including data output devices like screens, lights, audible transducers, tactile transducers and other output devices. User interface 201 is used to select electrodes to receive energy (electrodes 130 of carrier assembly 120), set power levels, durations, threshold levels and other ablation and other parameters, initiate power delivery, deactivate an alarm condition and other functions common to electronic medical devices. In a preferred embodiment, RF delivery unit 200 also includes cardiac mapping means, such that mapping attachment port 182 can be attached to RF delivery unit 200 avoiding the need for a separate piece of equipment in the system. In another preferred embodiment, RF delivery unit 200 can also deliver ultrasound and/or another form of energy, such energy delivered by one or more additional ablation elements integral to carrier assembly 120, additional ablation elements not shown. Applicable types of energy include but are not limited to: sound energy such as acoustic energy and ultrasound energy; electromagnetic energy such as electrical, magnetic, microwave and radiofrequency energies; thermal energy such as heat and cryogenic energies; chemical energy; light energy such as infrared and visible light energies; mechanical energy; radiation; and combinations thereof.

In a preferred embodiment, ablation catheter 100 includes an embedded identifier (ID), an uploadable electronic or other code, which can be used by RF delivery unit 200 to confirm compatibility and other acceptability of the specific catheter 100 with the specific RF delivery unit 200. The electronic code can be a bar code, not shown, on handle 110 which is read by RF delivery unit 200, an electronic code which is transferred to RF delivery unit 200 via a wired or wireless connection, not shown, or other identifying means, such as an RF tag embedded in handle 110. In another preferred embodiment, RF delivery unit 200 also includes an embedded ID, such as an ID which can be downloaded to catheter 100 for a second or alternative acceptability check. The embedded ID can also be used to automatically set certain parameters or certain parameter ranges, and can be used to increase safety by preventing inadvertent settings outside of an acceptable range for the specific catheter 100.

Handle 110 includes two push buttons, first button 116 and second button 117. These buttons can be used to perform one or more functions, and can work in cooperation with user input components of user interface 201 such that commands entered into user interface 201 set the action taken when either or both button 116 and button 117 are pressed. In a preferred embodiment, both button 116 and button 117 must be pressed simultaneously to deliver energy to one or more ablation elements of catheter 100. At the distal end of catheter shaft 101 is a circumferential band, band 104. Band 104 is preferably a visualization marker, such as a radiographic marker, ultrasound marker, electromagnetic marker, magnetic marker and combinations thereof. In an alternative embodiment, band 104 transmits or receives energy, such as when the marker is used as a ground or other electrode during an ablation. In another alternative embodiment, band 104 is an antenna used to determine the position of the distal end of catheter shaft 101 or the location of another component in relation to band 104. In another preferred embodiment, band 104 is used to store energy, such as capacitively stored energy that can be used to generate a magnetic field or to deliver ablation energy.

Referring now to FIG. 7, another preferred embodiment of ablation catheter 100 and ablation system of the present invention is illustrated comprising a catheter with a deflecting tip and a spiral tip carrier assembly. Catheter 100 includes carrier assembly 120 configured in a spiral tip configuration. Carrier assembly 120 includes a continuous wire construction such as a Nitinol wire that has been trained to be resiliently biased, at body temperature, in the spiral shape shown. Carrier assembly 120 includes multiple electrodes, mounted at equal distances from each other and electrically isolated to the wire of carrier assembly 120. Wires, attached to each electrode but not shown, are also electrically insulated from each other and travel along the spiral to the coupler 140, and then proximally to attachment means incorporated into handle 110. In an alternative embodiment, different patterns of electrodes are employed, such as a pattern of electrodes placed along a set of radial projections from the center of the spiral. Electrodes 130 may be conductive plates, coils, or other applicable structures for deploying energy, such as RF energy to tissue, and carrier assembly 130 can consist of electrodes with different construction materials and/or geometries.

Referring back to FIG. 7, each end of the spiral carrier assembly 120 is attached to coupler 140 which is sized to be slidably received within a lumen of distal end 102 of catheter shaft 101. Coupler 140 can be flexible or rigid, and may contain both rigid and flexible portions along its length. Coupler 140 may provide electrical connection means to connect wires extending from the handle to wires from carrier assembly 120 electrodes. The ends of spiral carrier assembly 120 can be attached to the outside of coupler 140, the inside of coupler 140 or both. Coupler 140 may include anti-rotation means, not shown but described in detail in reference to FIGS. 6 and 6a. Control shaft 140 may include a thru lumen, also not shown, such that ablation catheter 101 can be inserted over a guidewire (guidewire exit on handle 110 not shown).

Coupler 140 is mechanically attached to control shaft 150 which is mechanically attached to coupler 140. Control shaft 150 extends proximally to handle 110 and is operably connected to sliding knob 111, wherein sliding knob 111 can be distally advanced or proximally retracted in slot 112. Retraction of knob 111 from a distal position to a proximal position causes carrier assembly 120 to be constrained within a lumen at distal end 102 of catheter shaft 101, and advancement of knob 111 from a proximal position to a distal position causes carrier assembly 120 to extend beyond distal end 102 of catheter shaft 101, carrier assembly 120 resiliently expanding to its spiral shaped tip. In a preferred embodiment, knob 111 is operably connected to control shaft 150 via a cam, or set of gears, not shown, to provide a mechanical advantage in the distance traveled by control shaft 150, or the force exerted on control shaft 150.

Catheter shaft 101 is part of a steerable sheath, including pull wire 105 which is secured at one end to the distal end of control shaft 150 and at the other end is operably attached to knob 113, wherein sliding knob 113 can be distally advanced or proximally retracted in slot 114. The pull wire is operably connected to the control knob 113 so that sliding of the control knob pulls pull wire 105 to effectuate steering of the distal end 102 of control shaft 150. Retraction of knob 113 proximally causes distal end of control shaft 150 to deflect and advancement of knob 113 distally causes the distal end of control shaft 150 to straighten. Using knob 113, the operator can steer the carrier assembly 120 as needed to contact different areas of the atrium wall or other tissue surface. The pull wire 105 may be unsecured to the control shaft 150 along much of its length, or it may be embedded in the control shaft 150 wall or otherwise restrained to the control shaft 150. The entire distal end of the ablation catheter 100 may also be steered with pull wire 105, as the catheter shaft 101 is sufficiently flexible that it will deform along with the control shaft 150. In an additional or alternative embodiment, a second pull wire, not shown, is attached to the distal end of catheter shaft 101, this pull wire similarly attached to control means included in handle 101. In a preferred embodiment, knob 112 is operably connected to pull wire 105 via a cam, or set of gears, not shown, to provide a mechanical advantage in the distance traveled by pull wire 105, or the force exerted on pull wire 105. In an alternative or additional embodiment, a pull wire and handle control means can be connected to either catheter shaft 101 and/or control shaft 150 and/or coupler 140 and/or carrier assembly 120 at any location along their length, to cause a specific deflection pattern. In another preferred embodiment, the shaft to which the pull wire is attached includes multiple discrete levels of stiffness and/or variable levels of stiffness, near the attachment point, such that non-continuous bending occurs, i.e. bending with multiple radii or continuously variable radii.

Catheter shaft 101 includes flush port 170, which is configured to be attachable to a flushing syringe, used to flush blood and other contaminants from the lumen of an empty catheter shaft 101 (wherein control shaft 150, coupler 140 and carrier assembly 120 have been removed) or for flushing the space between control shaft 150 and the inner wall of catheter shaft 101. In a preferred embodiment, catheter shaft 101 is not connected to handle 110, such that handle 110 can be withdrawn, removing control shaft 150, coupler 140 and carrier assembly 120 from catheter shaft 101. This configuration is useful when these components are provided in a kit form, including combinations of different versions of these components, these different combinations made available to treat multiple patients, or a single patient.

Also depicted in FIG. 7 is a system of the present invention, including in addition to ablation catheter 100, RF delivery unit 200, a energy delivery apparatus of the present invention which connects to handle 110 with a multi-conductor cable 202 attached to RF attachment port 181. RF delivery unit 200 includes user interface 201, such as a user interface including data input devices like touch screens, buttons, switches, keypads, magnetic readers and other input devices; and also including data output devices like screens, lights, audible transducers, tactile transducers and other output devices. User interface 201 is used to select electrodes to receive energy (electrodes 130 of carrier assembly 120) and perform other functions as has been described in detail in reference to FIG. 6. In a preferred embodiment, RF delivery unit 200 can also deliver ultrasound and/or another form of energy, such energy delivered by one or more additional ablation elements integral to carrier assembly 120, additional ablation elements not shown. Applicable types of energy include but are not limited to: sound energy such as acoustic energy and ultrasound energy; electromagnetic energy such as electrical, magnetic, microwave and radiofrequency energies; thermal energy such as heat and cryogenic energies; chemical energy; light energy such as infrared and visible light energies; mechanical energy; radiation; and combinations thereof.

In a preferred embodiment, ablation catheter 100 and/or RF delivery unit 200 include an embedded identifier (ID), an uploadable or downloadable electronic or other code, which can be used by the system to confirm component compatibility and/or other acceptability of the specific catheter 100 with the specific RF delivery unit 200. The electronic code and some of its uses have been described in detail in reference to FIG. 6.

Referring now to FIGS. 8*a* and 8*b*, another preferred embodiment of the ablation catheter of the present invention is illustrated comprising a carrier assembly and control shaft that collectively consist of a continuous wire with one or more electrodes secured to a mid-portion of the wire. Depicted in FIGS. 8*a* and 8*b* is the distal end 102 of catheter shaft 101 which includes lumen 107, which extends from distal end 102 to a handle mounted on the proximal end of catheter shaft 101, handle not shown but similar in construction and function to the handles of previous figures. Included within lumen 107 is a wire assembly which comprises the control shaft and carrier assembly of the present invention. The wire assembly includes wire 129' with a first end and a second end, and wire 129" with a first end and a second end (both first ends not shown), such that both the first end of wire 129' and the first end of wire 129" exit the proximal end of catheter shaft 101, the mid-portion of the wire assembly comprising carrier assembly 120 which resides near the distal end 102 of the catheter shaft 101. The wire assembly has a length such that a when the mid-portion, carrier assembly 120, fully resides distal to the distal end 102 of catheter shaft 101 and wire 129' and wire 129" travel proximally within lumen 107 of catheter shaft 101, both the second end of wire 129' and the second end of wire 129" are proximal to the proximal end of the catheter shaft 101 (proximal end not shown).

Included in the carrier assembly 120 are four electrodes 130, noting that one or more electrodes should be considered within the scope of this application. Carrier assembly 120 includes a carrier wire 128, to which the electrodes 130 are mounted. Carrier wire 128 is preferably a non-conductive wire, such as a Teflon™ coated Nitinol wire, or a braided nylon line such that the electrodes can be electrically isolated from carrier wire 128. Alternatively, each electrode 130 can include an insulator. At each end of carrier assembly 120, carrier wire 128 transitions to wire 129' and wire 129" through transition point 122' and transition point 122" respectively. Depicted in FIGS. 8*a* and 8*b* carrier wire 128 has a smaller diameter than wire 129' and wire 129", such that wire 129' and wire 129" provides support of carrier assembly 120, in the configuration illustrated, such that carrier assembly 120 can be "pushed" into tissue while carrier wire 128 flexes in response to the tissue interaction. In alternative embodiments, various diameters, including continuous diameters and varied diameters can be used for each of the three components including a different diameter for each as well as a single diameter for the three, for example a single diameter Nitinol wire making up wire 129', transition point 122', carrier wire 128, transition point 122" and carrier wire 129". In an alternative embodiment, carrier wire 128 is a different material, with the same diameter or a different diameter, than one or more of wire 129' and wire 129". The carrier assembly 120 of FIGS. 8*a* and 8*b* is resiliently biased in a linear shape such that when carrier assembly 120 is fully exterior to lumen 107 of catheter shaft 101, as depicted in FIG. 8*a*, carrier wire 128 is relatively perpendicular to the axis of catheter shaft 101 and electrodes 130 are in a linear pattern. In an alternative embodiment, carrier wire 128 has a resiliently biased bowed shape, such as a bowed in shape or a bowed out shape. In another alternative embodiment, the electrodes 130 lie in multiple planes.

Carrier assembly 120 can be constrained within lumen 107 catheter shaft 101 by retracting wire 129', wire 129" or both. Utilizing control means incorporated into a handle, both not shown but described in detail in reference to previous figures, these advancements can be accomplished by an operator. Referring specifically to FIG. 8*b*, wire 129" has been retracted such that transition point 122' first enters lumen 107. Continued retraction of wire 129" causes carrier wire 128 and its electrodes 130 to enter lumen 107, followed by transition point 122' and a small segment of wire 129'. Alternatively or additionally, wire 129" can be retracted with a similar, symmetrical result, or both wires can be retracted in similar or dissimilar amounts wherein all described retractions cause carrier assembly 120 to be constrained with lumen 107 of catheter shaft. Performing the opposite step of advancing wire 129', wire 129" or both wires, such as with the same control that retracted the one or more wires, will cause carrier assembly 120 to advance past distal end 102 of catheter shaft 101, carrier assembly 120 then expanding to its resiliently biased condition. The ablation catheter of FIGS. 8a and 8b does not include the coupler of FIGS. 1 through 7, although in an alternative embodiment, two couplers can be incorporated onto the ends of carrier wire 128 and on to wire 129' and wire 129". In another alternative embodiment, the ablation catheter of FIGS. 8 and 8b can includes two wire assemblies, each including a separate carrier assembly each having ends attached to wires extending proximally. The multiple wire assemblies can have carrier assemblies with different or similar components and resiliently biased patterns of electrodes.

Figure 9:
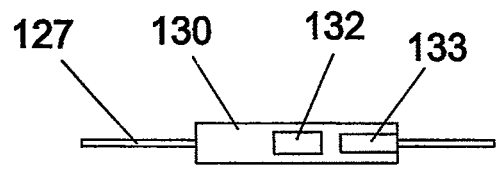
FIG. 9 illustrates an ablation element of an ablation catheter consistent with the present invention in which the ablation element includes an ultrasound crystal and a thermocouple.

Referring now to FIG. 9, an ablation element of the present invention is illustrated. Electrode 130, shown mounted to distal arm segment 127, such as a distal arm segment 127 of FIGS. 2 through 4. Included in electrode 130, is ultrasound crystal 132 and thermocouple 133. Wires, now shown, are attached to electrode 130, ultrasound crystal 132 and thermocouple 133, and travel along distal arm segment 127, to the lumen of the ablation catheter and proximally to the handle of the ablation catheter, all not shown. These wires interface with electronics within the handle and/or connected to a energy delivery apparatus, such as the RF delivery apparatus of FIGS. 6 and 7. The ultrasound crystal can be used to deliver ultrasound energy, simultaneous with or at a different time from RF energy being delivered to the tissue. Thermocouple 133 can be used to measure the temperature local to thermocouple 133 such as prior to, during or after the delivery of ablation energy. When an ablation is performed in the left atrium, such as the posterior wall of the left atrium, maintaining the tissue at a temperature below a threshold is needed. This wall is fairly thin, and the patient's esophagus lies immediately behind this wall. Ablation in this area entails a risk of perforating the atrial wall and the esophagus. In a preferred embodiment, information recorded from the thermocouple 133 is used to adjust energy delivery such as to start or stop one or more energy deliveries, or to increase, decrease, modify the frequency of, modify the bipolar or monopolar delivery means, or otherwise adjust the energy delivery based on a determined temperature or temperature information analysis. In another preferred embodiment, energy delivery is ceased when information from the thermocouple is one or more of: higher than a threshold, lower than a threshold such as lower than expected body temperature; or when the information is unavailable such as when the thermocouple is non-functional. In another preferred embodiment, in addition or alternative to the ultrasound energy, another form of energy is delivered by electrode 130. In another alternative embodiment, ultrasound crystal 133 and electrode 130 are two discrete components, located in proximity to one another on distal arm segment 127.

Figure 10:
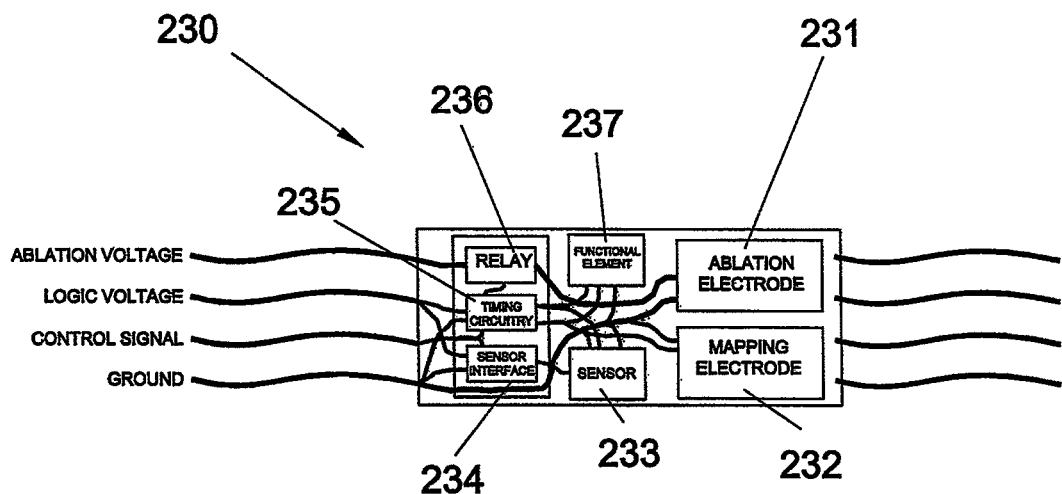
FIG. 10 illustrates an ablation element assembly of an ablation catheter consistent with the present invention in which the assembly is a semiconductor with integrated electronics.

Referring now to FIG. 10, an electrode assembly of the present invention is illustrated with electrode assembly 230 connected to power, signal and ground wires. Electrode assembly 230 includes a semiconductor substrate, such as a silicon substrate, in which is embedded numerous components fabricated using one or more of: integrated circuit fabrication machinery; Micro Electro-Mechanical Systems (MEMS) fabrication machinery; nano-system fabrication machines; other semi-conductor fabrication machinery; and combinations thereof. Electrode assembly 230 includes relay 236, which is configured to connect and disconnect ablation electrode 231 from an energy delivery apparatus connected to the ablation catheter to which electrode assembly 230 is a component. Other forms of relays can be integrated with multiple poles and multiple throws. Relays can connect and disconnect sources of signals and/or power. Multiple electrode assemblies 230 can be attached to a single, continuous ablation power wire and return ground greatly reducing the number of wires needed to travel from the proximal handle to the carrier assembly. Individual, or combination control of each ablation electrode 231 can be provided however, through opening or closing of relay 236 which is accomplished via timing circuitry 235. Control signals are sent to the embedded electronics of timing circuitry 235 such that digital or analog information can be transferred into logic that open and closed each relay 236, at precise times, and utilizing specific electronic identifiers embedded in each electrode assembly 230, can independently control all of the components of electrode assembly 230. Timing circuitry 235 can interpret signals that it receives from another electrode assembly 230, or a device external to the patient. Timing circuitry 235 can produce pulse-width modulated opening and closing of relay 236, or other sophisticated timing patterns which may be specific to the construction or makeup of electrode assembly 230.

Electrode assembly 230 further includes sensor 233, which can be an individual sensor or bank of multiple sensors such as a sensor to sense one or more of: chemical activity, light characteristic such as intensity or wavelength, electrical activity, pH, temperature, pressure, fluid flow or other physiologic parameter. Electrode assembly 230 further includes sensor interface 234 which includes various electronic components and circuitry such as circuitry created in various doping and other integrated circuit building processes used in a semiconductor substrate such as silicon. The information provided by sensor 233 can be processed by sensor interface 234 and/or by circuitry included in a proximal handle or energy delivery apparatus. This information can be used to start, stop, increase, decrease or otherwise modify energy delivery or control another function of electrode assembly 230 or another function of the ablation catheter of the present invention.

Electrode assembly 230 further includes mapping electrode 232 which provides recording of electrical signals of the heart, such as signals used to identify rotors to be ablated during the procedure. In an alternative embodiment, ablation electrode 231 is used to record the electrical signals of the heat. Electrode assembly 230 further includes functional element 237, which may include integrated circuit components described above, as well as MEMS or nano-machine components that are well known to being integrated into semiconductor substrates using the appropriate machinery. A preferred embodiment of FIG. 10 is the incorporation of a MEMS valve which is used to control fluid flow, such as fluid flow to cool electrode assembly 230 and/or ablation electrode 231 or a valve used to control the flow of or release cryogenic fluid used to ablate tissue. In another preferred embodiment, a MEMS pump can be used to pump fluid, such as a drug or other chemical used to chemically create a lesion in tissue. In another preferred embodiment a MEMS linear actuator is incorporated to deploy one or more microneedles used to deliver a fluid such as the described drug. In another preferred embodiment, microcontroller or microprocessor circuitry is embedded in a semiconductor portion of electrode assembly 230 such that sophisticated signal processing and/or controlled loop delivery of energy can be configured such that complicated energy delivery can be used with one or more less sophisticated energy delivery apparatus.

Multiple semiconductor portions can be integrated into electrode assembly 230, such as portions which are connected with an insulating material and/or a flexible material providing a flexible joint between rigid portions of electrode assembly 230. Utilizing semiconductor technology and/or MEMS or other semiconductor fabrication means, numerous functions can be incorporated into electrode assembly 230 to improve therapeutic benefit of the procedure, provide enhanced safety to the procedure, or provide other therapeutic or non-therapeutic benefit to the patient or the operator of the system. In an alternative embodiment, the electrode assembly further comprises a cooling element, such as a heat sink, not shown.

Referring now to FIG. 11, an end view of another preferred embodiment of the carrier assembly of the present invention is illustrated comprising a carrier assembly in a spiral tip configuration. Carrier assembly 120, shown in its resiliently expanded condition, includes a single wire, carrier wire 128 which has a first end 143 and a second end 144. First end 143 in attached to coupler 140, travels radially out from the center axis of catheter shaft 101 and carrier wire 128 begins to travel along a continuously increasing radius creating a multiple loop spiral. After the creation of six spirals, carrier wire 128 travels radially in toward the central axis of catheter shaft 101, such that second end 144 also attached to coupler 140. Referring to FIG. 11a, a side view of the carrier assembly 120 of FIG. 11 is depicted in its fully expanded condition wherein the spirals lie in multiple planes. FIG. 11b illustrates a side view of an alternative embodiment of the carrier assembly of FIG. 11, in which the spirals of the carrier assembly 120, depicted in its fully expanded condition, lie in a relatively single plane. The spirals of both FIGS. 11a and 11b include one or more electrodes 130. The length and diameter of the carrier wire 128, as well as the size of the electrodes, are chosen such that the control shaft 140, which is connected to carrier assembly 120 by coupler 140, can be retracted such that the entire carrier assembly 120 appropriately folds and is constrained within a lumen of catheter shaft 101.

Another alternative embodiment of the ablation catheter of the present invention is also depicted in FIG. 11a wherein means of anchoring the carrier assembly 120 to the tissue to be ablated is provided. In the center portion of the spiral, suction port 153 is provided. Suction port 153 is fluidly attached to control shaft lumen 152 which is also fluidly attached to a port on the proximal handle, not shown. A vacuum apparatus, such as a locking syringe, also not shown, when attached to the proximal handle, and the carrier assembly 120 is brought in contact with tissue; and the vacuum is generated such as drawing back the plunger of the syringe and locking the plunger, will cause the carrier assembly to be anchored to the tissue. This anchoring embodiment is of particular value when first performing an assessment such as a mapping procedure or other analysis from electrodes or other sensors; after which an ablation is to be performed in the same location. In an alternative embodiment, suction port 153 is replaced with a deployable tissue penetrating anchor, such as a corkscrew wire or barbed wire.

Referring now to FIG. 12, an end view of another preferred embodiment of the carrier assembly of the present invention is illustrated comprising a carrier assembly with multiple wires, each with a proximal end and a distal end, wherein each proximal end and each distal end is secured to coupler 140. Carrier assembly 120 includes multiple carrier wires 128, each with a flower petal or petaloid shape when fully expanded. Each end of carrier wire 128 is secured to coupler 140, which is attached to a control shaft, not shown. The control shaft is sized to be slidingly received by catheter shaft 101. Carrier wires 128 include one or more electrodes, and one or more carrier wires 128 may include no electrodes, all electrodes not shown. The carrier wire length and diameter, as well as the size of the electrodes, are chosen such that the control shaft can be retracted such that the entire carrier assembly 120 appropriately folds and is constrained within a lumen of catheter shaft 101. In an alternative embodiment, each proximal end of carrier wire assembly is attached to coupler 140, and each distal end is attached near the distal end of catheter shaft 101, such as within the lumen of catheter shaft 101, such that retraction of the control shaft causes coupler 140 and carrier assembly 120 to reside within a lumen of catheter shaft 101.

It should be understood that numerous other configurations of the systems, devices and methods described herein can be employed without departing from the spirit or scope of this application. It should be understood that the system includes multiple functional components, such as the ablation catheter and the energy delivery apparatus. The ablation catheter consists of a catheter shaft, a carrier assembly for providing electrodes in a resiliently biased configuration, a control shaft for deploying and withdrawing the carrier assembly, and a coupler for attaching the control shaft to the carrier assembly. The carrier assembly is a support structure which is shiftable from a storage or confined configuration, such as a radially constrained configuration, to a deployed or expanded configuration. The carrier assembly can includes wires, ribbons, cables and struts, made of either metals, non-metals or combinations of both. The carrier assembly can be constructed of one or more materials, including both metals and non-metals. Typical metals chosen for carrier assembly construction include but are not limited to: stainless steel, Nitinol, Elgiloy™, other alloys and combinations thereof.

The ablation catheter of the present invention may include a steerable outer sheath, or may work in conjunction as a system with a separate steerable outer sheath. One or more tubular components of the ablation catheter may be steerable such as with the inclusion of a controllable pull wire at or near the distal end. The ablation catheter of the present invention may be inserted over the wire, such as via a lumen within one of the tubular conduits such as within a lumen of the tubular body member or control shaft, or alternatively the catheter may include a rapid exchange sidecar at or near its distal end, consisting of a small projection with a guidewire lumen therethrough. A guidewire lumen may be included solely for the guidewire, or may provide other functions such as a vacuum lumen for an integral suction port integrated at the distal portion of the carrier assembly.

The ablation catheter of the present invention further includes ablation elements. In preferred embodiments, one or more ablation elements are electrodes configured to deliver RF energy. Other forms of energy, alternative or in addition to RF, may be delivered, including but not limited to: acoustic energy and ultrasound energy; electromagnetic energy such as electrical, magnetic, microwave and radiofrequency energies; thermal energy such as heat and cryogenic energies; chemical energy; light energy such as infrared and visible light energies; mechanical energy; radiation; and combinations thereof. One or more ablation elements may comprise a drug delivery pump or a device to cause mechanical tissue damage such as a forwardly advanceable spike or needle. The ablation elements can deliver energy individually, in combination with or in serial fashion with other ablation elements. The ablation elements can be electrically connected in parallel, in series, individually, or combinations thereof. The ablation catheter may include cooling means to prevent undesired tissue damage and/or blood clotting. The ablation elements may be constructed of various materials, such as plates of metal and coils of wire for RF energy delivery. The electrodes can take on various shapes including shapes used to focus energy such as a horn shape to focus sound energy, and shapes to assist in cooling such as a geometry providing large surface area. Electrodes can vary within a single carrier assembly, such as a spiral array of electrodes or a umbrella tip configuration wherein electrodes farthest from the central axis of the catheter have the largest major axis. Wires and other flexible conduits are attached to the ablation elements, such as electrical energy carrying wires for RF electrodes or ultrasound crystals, and tubes for cryogenic delivery.

The ablation elements requiring electrical energy to ablate require wired connections to an electrical energy power source such as an RF power source. In configurations with large numbers of electrodes, individual pairs of wires for each electrode may be bulky and compromise the cross-sectional profile of the ablation catheter. In an alternative embodiment, one or more electrodes, connected in serial fashion such that a reduced number of wires, such as two wires, can be attached to two or more electrodes, include switching means such that while a first electrode is powered, the remaining electrodes do not transmit ablative energy. Switching means may be a thermal switch, such that as a first electrodes heats up, a single pole double throw switch change state disconnecting power from that electrode and attaching power to the next electrode in the serial connection. This integral temperature switch may have a first temperature to disconnect the electrode, and a second temperature to reconnect the electrode wherein the second temperature is lower than the first temperature, such as a second temperature below body temperature. In an alternative embodiment, each electrode is constructed of materials in their conductive path such that as when the temperature increased and reached a predetermined threshold, the resistance abruptly decreased to near zero, such that power dissipation, or heat, generated by the electrode was also near zero, and more power could be delivered to the next electrode incorporating the above switching means.

The ablation catheter of the present invention preferably includes a handle activating or otherwise controlling one or more functions of the ablation catheter. The handle may include various knobs, such as rotating or sliding knobs which are operably connected to advanceable conduits, or are operably connected to gear trains or cams which are connected to advanceable conduits. These knobs, such as knobs use to deflect a distal portion of a conduit, or to advance or retract the carrier assembly, preferably include a reversible locking mechanism such that a particular tip deflection or deployment amount can be maintained through various manipulations of the system.

The ablation catheter may include one or more sensors, such as sensors used to detect chemical activity; light; electrical activity; pH; temperature; pressure; fluid flow or another physiologic parameter. These sensors can be used to map electrical activity, measure temperature, or gather other information that may be used to modify the ablation procedure. In a preferred embodiment, one or more sensors, such as a mapping electrode, can also be used to ablate tissue.

Numerous components internal to the patient, such as the carrier assembly or electrodes, may include one or more visual markers such as radiopaque markers visible under fluoroscopy, or ultrasound markers.

Selection of the tissue to be ablated may be based on a diagnosis of aberrant conduit or conduits, or based on anatomical location. RF energy may be delivered first, followed by another energy type in the same location, such as when a single electrode can deliver more than one type of energy, such as RF and ultrasound energy. Alternatively or additionally, a first procedure may be performed utilizing one type of energy, followed by a second procedure utilizing a different form of energy. The second procedure may be performed shortly after the first procedure, such as within four hours, or at a later date such as greater than twenty-four hours after the first procedure. Numerous types of tissue can be ablated utilizing the devices, systems and methods of the present invention. For example, the various aspects of the invention have application in procedures for ablating tissue in the prostrate, brain, gall bladder, uterus, other organs and regions of the body, and a tumor, preferably regions with an accessible wall or flat tissue surface. In the preferred embodiment, heart tissue is ablated, such as left atrial tissue.

In another preferred embodiment of the system of the present invention, an ablation catheter and a heat sensing technology are included. The heat sensing technology, includes sensor means that may be placed on the chest of the patient, the esophagus or another area in close enough proximity to the tissue being ablated to directly measure temperature effects of the ablation, such as via a temperature sensor, or indirectly such as through the use of an infrared camera. In the described system, when a temperature or a surrogate temperature reaches a threshold, such as an adjustable threshold, the ablation energy is reduced or stopped, to one or more ablation elements. The threshold will depend on the location of the sensor means, as well as where the ablation energy is being delivered. The threshold may be adjustable, and may be automatically configured.

Numerous kit configurations are also to be considered within the scope of this application. An ablation catheter is provided with multiple carrier assemblies. These carrier assemblies can be removed for the tubular body member of the catheter, or may include multiple tubular body members in the kit. The multiple carrier assemblies can have different patterns, different types or amounts of electrodes, and have numerous other configurations including compatibility with different forms of energy.

Though the ablation device has been described in terms of its preferred endocardial and transcutaneous method of use, the array may be used on the heart during open heart surgery, open chest surgery, or minimally invasive thoracic surgery. Thus, during open chest surgery, a short catheter or cannula carrying the carrier assembly and its electrodes may be inserted into the heart, such as through the left atrial appendage or an incision in the atrium wall, to apply the electrodes to the tissue to be ablated. Also, the carrier assembly and its electrodes may be applied to the epicardial surface of the atrium or other areas of the heart to detect and/or ablate arrhythmogenic foci from outside the heart.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. A method of ablating cardiac tissue of a patient the method comprising:

advancing an ablation catheter into contact with a target tissue in the patient's heart, the ablation catheter comprising a plurality of electrodes in electrical communication with an RF generator having a user interface;

placing an indifferent electrode in contact with the patient;

selecting a first energy delivery mode from the user interface;

delivering RF energy to at least one of the electrodes of the ablation catheter in the first energy delivery mode to ablate the target tissue;

assessing the condition of the target tissue;

selecting a second energy delivery mode from the user interface that is different than the first energy delivery mode; and delivering RF energy to at least one of the electrodes of the ablation catheter in the second energy delivery mode to ablate the target tissue, wherein the selecting step comprises selecting from the group consisting of a monopolar only energy delivery mode, a bipolar only delivery mode, and a combined bipolar/monopolar energy delivery mode.

2. The method of claim 1 wherein the target tissue is a first tissue location within the patient's heart, the method further comprising:

advancing the ablation catheter into contact with a second target tissue in the patient's heart;

selecting an energy delivery mode from the user interface that is different than one of the first and second energy delivery modes; and delivering RF energy to at least one of the electrodes of the ablation catheter in the different energy delivery mode to ablate the second target tissue.

3. The method of claim 1 further comprising measuring a temperature of the at least one of the electrodes.

4. The method of claim 1, wherein the energy delivery mode selected in the first selecting step is monopolar only energy delivery mode.

5. The method of claim 4 wherein the energy delivery mode selected in the second selecting step is bipolar only energy delivery mode.

6. The method of claim 1 wherein assessing the condition of the target tissue includes assessing an electrical signal of the target tissue.

7. The method of claim 3 further comprising modifying the delivery of RF energy based at least in part on the measured temperature.

8. The method of claim 1 further comprising:

delivering no energy to any of the electrodes for a period of time substantially equal to at least one of the period of time for delivery of the first and second energy delivery modes.

9. A method of ablating cardiac tissue of a patient, the method comprising:

delivering RF energy in monopolar only energy delivery mode to target tissue for a first period of time to ablate the target tissue;

delivering RF energy in bipolar only energy delivery mode to target tissue for a second period of time to ablate the target tissue; and delivering no energy to the target tissue for a third period of time, the first, second, and third periods of time being approximately the same.

10. A method of ablating cardiac tissue of a patient, the method comprising:

delivering RF energy in a first energy delivery mode to target tissue for a first period of time to ablate the target tissue;

delivering RF energy in a second energy delivery mode to target tissue for a second period of time to ablate the target tissue; and delivering no energy to the target tissue for a third period of time, the first, second, and third periods of time being approximately the same and one of the first and second energy delivery modes being a combination of monopolar and bipolar energy delivery modes.

* * * * *